US011786197B2

(12) United States Patent
Bettoyashiki et al.

(10) Patent No.: US 11,786,197 B2
(45) Date of Patent: Oct. 17, 2023

(54) RADIATION INTENSITY ESTIMATION APPARATUS, METHOD OF OPERATING RADIATION INTENSITY ESTIMATION APPARATUS, OPERATION PROGRAM FOR RADIATION INTENSITY ESTIMATION APPARATUS, AND RADIOGRAPHY SYSTEM

(71) Applicant: FUJIFILM CORPORATION, Tokyo (JP)

(72) Inventors: Akihito Bettoyashiki, Kanagawa (JP); Ryo Imamura, Kanagawa (JP); Kazuhiro Makino, Kanagawa (JP); Takeyasu Kobayashi, Kanagawa (JP); Naoyuki Nishino, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 448 days.

(21) Appl. No.: 17/179,403

(22) Filed: Feb. 19, 2021

(65) Prior Publication Data
US 2021/0275120 A1   Sep. 9, 2021

(30) Foreign Application Priority Data

Mar. 6, 2020   (JP) ................. 2020-039224

(51) Int. Cl.
*A61B 6/00* (2006.01)
*G06T 7/521* (2017.01)
(Continued)

(52) U.S. Cl.
CPC ............ *A61B 6/4405* (2013.01); *A61B 6/463* (2013.01); *G06F 18/24* (2023.01); *G06N 5/04* (2013.01);
(Continued)

(58) Field of Classification Search
None
See application file for complete search history.

(56) References Cited

U.S. PATENT DOCUMENTS

2012/0051513 A1* 3/2012 Nishino ............... A61B 6/4283
378/63
2016/0302758 A1* 10/2016 Horiuchi ............... A61B 6/465
(Continued)

FOREIGN PATENT DOCUMENTS

JP   2005-253689 A   9/2005
JP   2014-236798 A   12/2014
(Continued)

OTHER PUBLICATIONS

English language translation of the following: Office action dated Jan. 17, 2023 from the JPO in a Japanese patent application No. 2020-039224 corresponding to the instant patent application. This office action translation is submitted now in order to supplement the understanding of the cited references which are being disclosed in the instant Information Disclosure Statement.
(Continued)

*Primary Examiner* — Marcus H Taningco
(74) *Attorney, Agent, or Firm* — SOLARIS Intellectual Property Group, PLLC

(57) ABSTRACT

A CPU of a console comprises a color image acquisition unit, a distance image acquisition unit, a specification unit, and an estimation unit. The color image acquisition unit acquires a color image, in which a patient and a periphery of the patient are captured, from a visible light camera. The distance image acquisition unit acquires a distance image indicating a distance between a radiation tube and an object, from a TOF camera. The specification unit specifies a kind of the object in the color image. The estimation unit estimates intensity of radiation in an environment captured in the color image based on reference information including
(Continued)

the distance image and a specification image as a specification result of the kind of the object.

20 Claims, 25 Drawing Sheets

(51) Int. Cl.
| | | |
|---|---|---|
| G06T 7/00 | (2017.01) |
| G06N 5/04 | (2023.01) |
| G06N 20/00 | (2019.01) |
| G06V 40/10 | (2022.01) |
| G06F 18/24 | (2023.01) |
| G06V 10/764 | (2022.01) |
| G06V 10/82 | (2022.01) |

(52) U.S. Cl.
CPC .......... *G06N 20/00* (2019.01); *G06T 7/0014* (2013.01); *G06T 7/521* (2017.01); *G06V 10/764* (2022.01); *G06V 10/82* (2022.01); *G06V 40/10* (2022.01); *G06T 2207/10024* (2013.01); *G06T 2207/10028* (2013.01); *G06T 2207/20081* (2013.01); *G06V 2201/03* (2022.01)

(56) References Cited

U.S. PATENT DOCUMENTS

| | | | |
|---|---|---|---|
| 2018/0010903 A1* | 1/2018 | Takao | G01S 7/4816 |
| 2018/0070911 A1* | 3/2018 | Franklin | A61B 6/487 |
| 2021/0169438 A1* | 6/2021 | Ruff | A61B 6/4417 |
| 2021/0207952 A1* | 7/2021 | Fujiwara | H04N 13/128 |
| 2022/0287675 A1* | 9/2022 | Ruff | A61B 6/547 |
| 2023/0094681 A1* | 3/2023 | Lambin | A61N 5/1031 |
| | | | 600/1 |

FOREIGN PATENT DOCUMENTS

| | | |
|---|---|---|
| JP | 2015-134108 A | 7/2015 |
| WO | 2020-028704 A1 | 2/2020 |

OTHER PUBLICATIONS

English language translation of the following: Decision of Refusal dated Jun. 13, 2023 from the JPO in a Japanese patent application No. 2020-039224 corresponding to the instant patent application.

* cited by examiner

| IMAGING MENU | | IRRADIATION CONDITION |
|---|---|---|
| FRONT CHEST DECUBITUS | BODY SHAPE SMALL | TUBE VOLTAGE 150 kV  TUBE CURRENT 20 mA  IRRADIATION TIME 10 ms |
| FRONT CHEST DECUBITUS | BODY SHAPE MEDIUM | TUBE VOLTAGE 150 kV  TUBE CURRENT 25 mA  IRRADIATION TIME 10 ms |
| FRONT CHEST DECUBITUS | BODY SHAPE LARGE | TUBE VOLTAGE 150 kV  TUBE CURRENT 30 mA  IRRADIATION TIME 10 ms |
| ⋮ | | ⋮ |

<LEARNING PHASE>

RADIATION INTENSITY ESTIMATION APPARATUS, METHOD OF OPERATING RADIATION INTENSITY ESTIMATION APPARATUS, OPERATION PROGRAM FOR RADIATION INTENSITY ESTIMATION APPARATUS, AND RADIOGRAPHY SYSTEM

CROSS-REFERENCE TO RELATED APPLICATIONS

The present application claims priority under 35 U.S.C. § 119 to Japanese Patent Application No. 2020-039224, filed on Mar. 6, 2020. The above application is hereby expressly incorporated by reference, in its entirety, into the present application.

BACKGROUND

1. Technical Field

A technique of the present disclosure relates to a radiation intensity estimation apparatus, a method of operating a radiation intensity estimation apparatus, an operation program for a radiation intensity estimation apparatus, and a radiography system.

2. Description of the Related Art

In a medical site, there is a concern about careless exposure to a person (an operator, such as a radiographer, an attendant of a patient, or the like) other than an imaging target (a patient or the like) of radiography. Accordingly, JP2015-134108A describes a technique that displays an estimated irradiation region where irradiation of radiation is estimated before radiography in a radiography system, which has a C-arm, in which a radiation tube configured to emit radiation and a radiographic image detection device configured to output a radiographic image are disposed to face each other, and is stationary in an imaging room.

In JP2015-134108A, as the estimated irradiation region of radiation, an estimated irradiation region of scattered radiation scattered by an imaging target or the like is displayed in addition to an estimated irradiation region of direct radiation emitted from the radiation tube. The estimated irradiation region of the direct radiation is derived from information, such as a position of the radiation tube and an opening degree of an emission opening of an irradiation field limiter (also referred to as a collimator). The estimated irradiation region of scattered radiation is derived from information, such as a position of a bed on which the imaging target is laid, a size of the imaging target, and a tube voltage applied to the radiation tube. The position of the bed is preset. The estimated irradiation region of scattered radiation is specifically a region where scattered radiation of predetermined intensity or more is estimated to be generated. Furthermore, JP2015-134108A also describes an example where a plurality of pieces of standard arrangement information of an object present in the periphery of the imaging target are preset, and the estimated irradiation region of scattered radiation with respect to the estimated irradiation region of direct radiation is calculated based on the standard arrangement information.

SUMMARY

Incidentally, a mobile radiation generation apparatus is known as a radiation generation device comprising a radiation tube. The mobile radiation generation apparatus has, for example, a configuration in which a body portion having a radiation generation unit including the radiation tube is mounted on a carriage having wheels, and is movable by the carriage. The mobile radiation generation apparatus is used in so-called round imaging for imaging the imaging target while visiting patient's rooms making use of mobility. Alternatively, the mobile radiation generation apparatus is also used in imaging in an emergency room. Furthermore, the mobile radiation generation apparatus can also be carried in an operation room and used in the middle of an operation. In addition, the mobile radiation generation apparatus can also be carried in an outdoor disaster site and used in emergency.

The radiography system stationary in the imaging room described in JP2015-134108A is a stationary type, and thus, the arrangement of the object present in the periphery of the imaging target is approximately determined for each installation place of the radiography system. For this reason, in a case where information (the position of the bed and the standard arrangement information) indicating an object present in the periphery of the imaging target and how far the object and the radiation tube are separated from each other is preset, the intensity of the scattered radiation can be measured.

In contrast, in the radiography system comprising the mobile radiation generation apparatus, the distance between an object present in the periphery of the imaging target and the radiation tube changes due to the specificity of the application of the mobile radiation generation apparatus that an imaging place is not decided to one place. For this reason, as in JP2015-134108A, information indicating an object present in the periphery of the imaging target and how far the object and the radiation tube are separated from each other cannot be preset. Accordingly, in the radiography system comprising the mobile radiation generation apparatus, even though the technique described in JP2015-134108A is applied, the intensity of radiation cannot be appropriately estimated.

An object of the technique of the present disclosure provides a radiation intensity estimation apparatus, a method of operating a radiation intensity estimation apparatus, an operation program for a radiation intensity estimation apparatus, and a radiography system capable of appropriately estimating an intensity of radiation according to circumstances in the periphery of an imaging target changing depending on an imaging place in a case where a mobile radiation generation apparatus is used.

To achieve the above-described object, the present disclosure provides a radiation intensity estimation apparatus that is used in a mobile radiation generation apparatus, which has a radiation generation unit including a radiation tube configured to emit radiation and is movable by a carriage having wheels, and estimates an intensity of radiation before radiography. The radiation intensity estimation apparatus comprises at least one processor. The processor is configured to execute optical image acquisition processing of acquiring an optical image, in which an imaging target of the radiography and a periphery of the imaging target are captured, from a camera, distance information acquisition processing of acquiring distance information indicating a distance between the radiation tube and an object, from a distance sensor, specification processing of specifying a kind of the object in the optical image, and estimation processing of estimating the intensity of the radiation in an environment captured in the optical image based on reference information including the distance information and a specification result of the kind of the object.

It is preferable that the reference information further includes an irradiation condition of the radiation and opening degree information of an emission opening of an irradiation field limiter configured to limit an irradiation field of the radiation.

It is preferable that the processor is configured to control display of an estimation result of the intensity.

It is preferable that the processor is configured to display the optical image and the estimation result together.

It is preferable that the optical image is a color image, the estimation result is an intensity map indicating a level of the intensity of each divided region obtained by dividing the optical image, and the processor is configured to display the intensity map on the color image in a superimposed manner.

It is preferable that the processor is configured to display the estimation result through a display mounted in the mobile radiation generation apparatus and configured to display a radiographic image.

It is preferable that the processor is configured to display the estimation result through a display of a terminal carried by an operator.

It is preferable that the processor is configured to display the estimation result through a projector.

It is preferable that the processor is configured to update the display of the estimation result at a predetermined time interval.

It is preferable that the processor is configured to not update the display of the estimation result in a case where an amount of temporal change of the estimated intensity is less than a predetermined threshold value, and to update the display of the estimation result in a case where the amount of change is equal to or greater than a threshold value.

It is preferable that the processor is configured to output a warning in a case where a person other than the imaging target is present in a region where the estimated intensity is equal to or greater than a predetermined threshold value.

It is preferable that the processor is configured to use a first machine learning model with the optical image as input data and the specification result of the kind of the object as output data.

It is preferable that the processor is configured to use a second machine learning model with the reference information as input data and the estimation result of the intensity as output data.

The present disclosure provides a method of operating a radiation intensity estimation apparatus that is used in a mobile radiation generation apparatus, which has a radiation generation unit including a radiation tube configured to emit radiation and is movable by a carriage having wheels, and estimates an intensity of radiation before radiography. The method comprises an optical image acquisition step of acquiring an optical image, in which an imaging target of the radiography and a periphery of the imaging target are captured, from a camera, a distance information acquisition step of acquiring distance information indicating a distance between the radiation tube and an object, from a distance sensor, a specification step of specifying a kind of the object in the optical image, and an estimation step of estimating the intensity of the radiation in an environment captured in the optical image based on reference information including the distance information and a specification result of the kind of the object.

The present disclosure provides an operation program for a radiation intensity estimation apparatus that is used in a mobile radiation generation apparatus, which has a radiation generation unit including a radiation tube configured to emit radiation and is movable by a carriage having wheels, and estimates an intensity of radiation before radiography. The operation program causes a computer to function as an optical image acquisition unit that acquires an optical image, in which an imaging target of the radiography and a periphery of the imaging target are captured, from a camera, a distance information acquisition unit that acquires distance information indicating a distance between the radiation tube and an object, from a distance sensor, a specification unit that specifies a kind of the object in the optical image, and an estimation unit that estimates the intensity of the radiation in an environment captured in the optical image based on reference information including the distance information and a specification result of the kind of the object.

The present disclosure provides a radiography system comprising a mobile radiation generation apparatus that has a radiation generation unit including a radiation tube configured to emit radiation and is movable by a carriage having wheels, a camera that images an imaging target of radiography and a periphery of the imaging target and outputs an optical image, a distance sensor that detects distance information indicating a distance between the radiation tube and an object, and at least one processor, in which the processor is configured to execute, before radiography, optical image acquisition processing of acquiring the optical image from the camera, distance information acquisition processing of acquiring the distance information from the distance sensor, specification processing of specifying a kind of the object in the optical image, and estimation processing of estimating the intensity of the radiation in an environment captured in the optical image based on reference information including the distance information and a specification result of the kind of the object.

It is preferable that the camera and the distance sensor are provided in the radiation generation unit.

It is preferable that the camera sequentially outputs the optical image in compliance with a preset frame interval, and the distance sensor sequentially detects the distance information in compliance with a detection interval according to the frame interval and outputs the distance information.

It is preferable that the camera is a visible light camera that outputs a color image as the optical image.

It is preferable that the distance sensor is a distance measurement camera that measures the distance to the object using a time-of-flight method.

According to the technique of the present disclosure, it is possible to provide a radiation intensity estimation apparatus, a method of operating a radiation intensity estimation apparatus, an operation program for a radiation intensity estimation apparatus, radiography system capable of appropriately estimating an intensity of radiation according to circumstances in the periphery of an imaging target changing depending on an imaging place in a case where a mobile radiation generation apparatus is used.

BRIEF DESCRIPTION OF THE DRAWINGS

Exemplary embodiments according to the technique of the present disclosure will be described in detail based on the following figures, wherein.

DETAILED DESCRIPTION

First Embodiment

Figure 1:
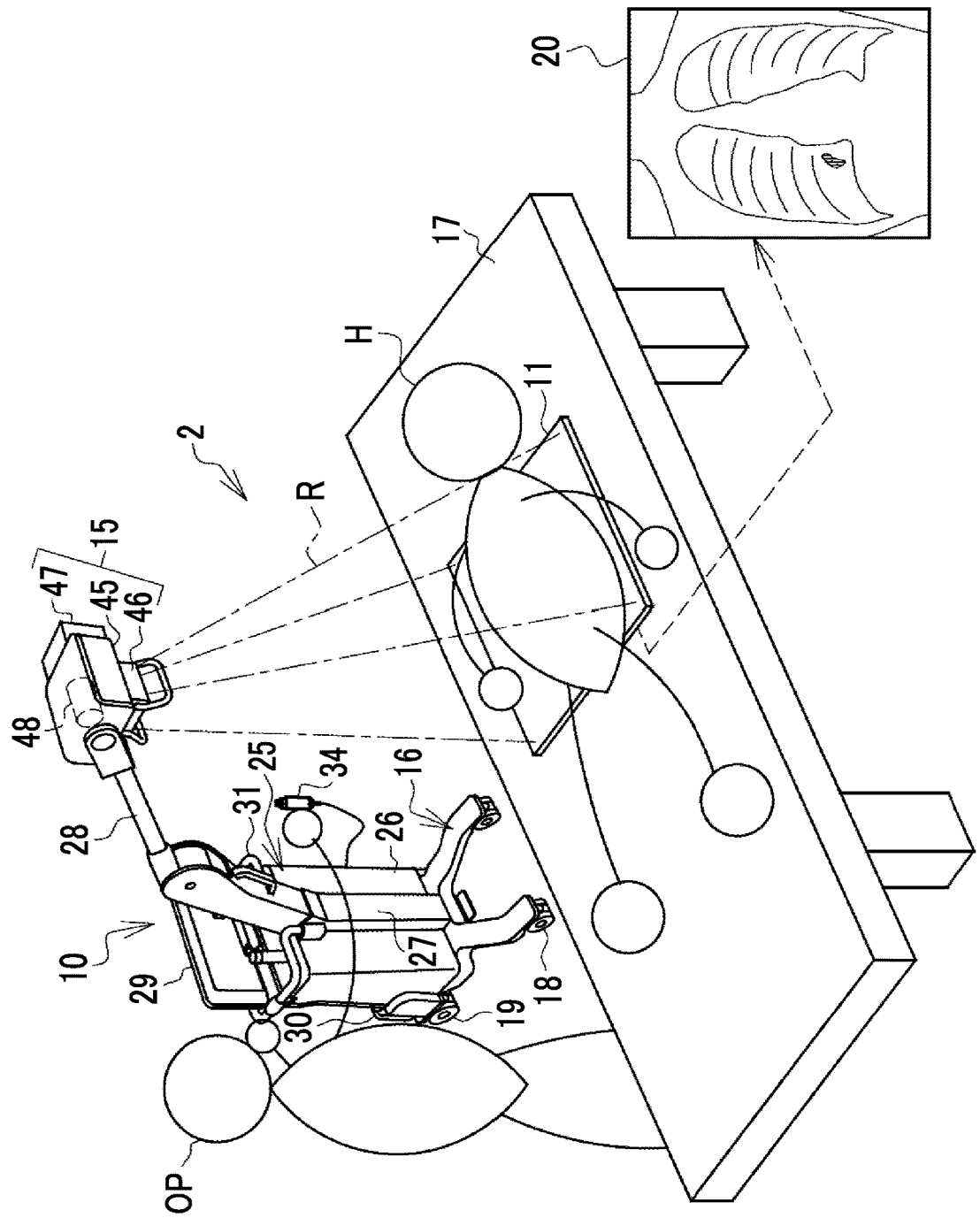
FIG. 1 is a diagram showing a manner of imaging using a radiography system.
Figure 2:
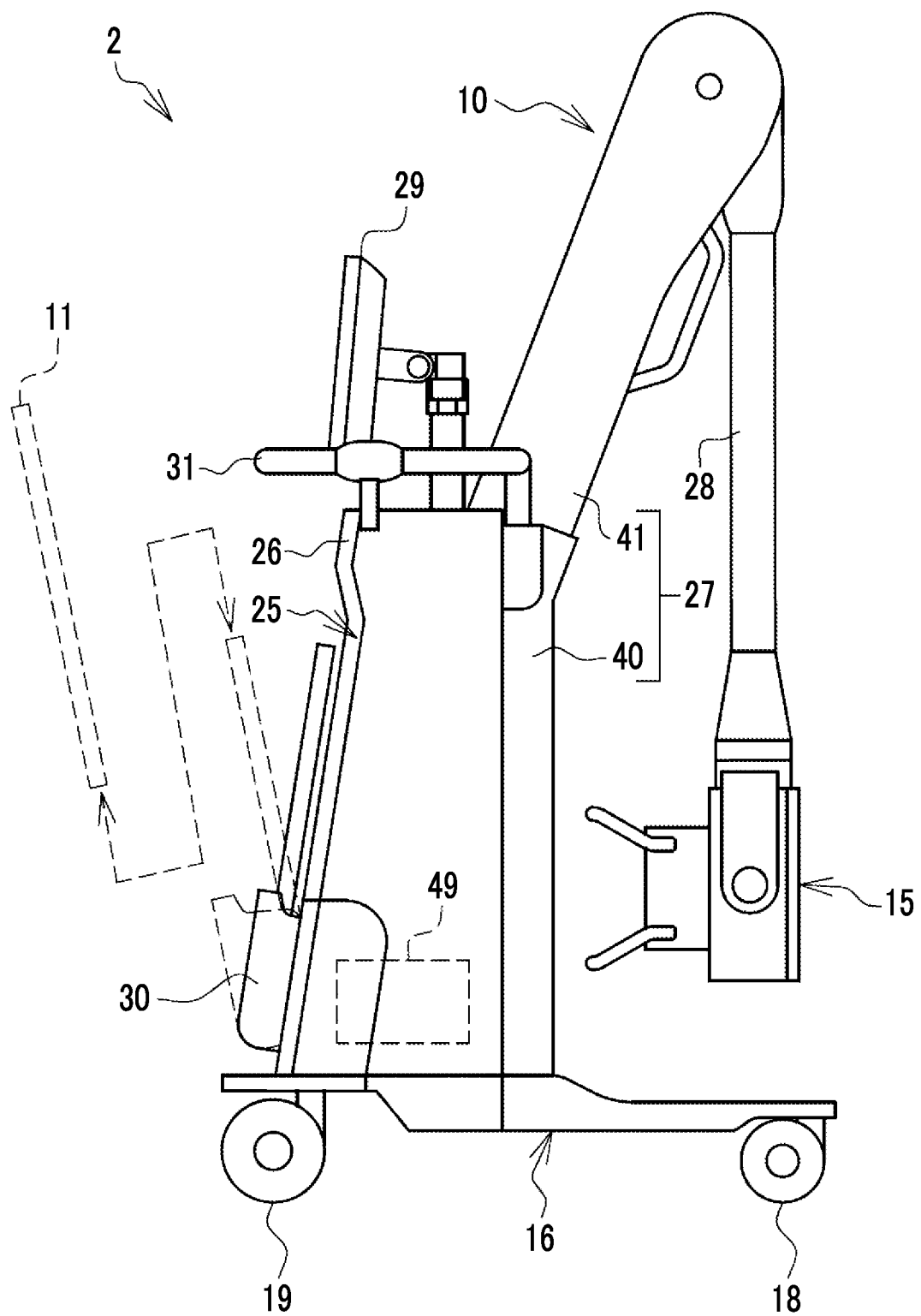
FIG. 2 is a diagram showing a radiography system.

In FIGS. 1 and 2, a radiography system 2 comprises a mobile radiation generation apparatus 10 and an electronic cassette 11. The mobile radiation generation apparatus 10 has a radiation generation unit 15 and a carriage 16. The radiation generation unit 15 emits radiation R toward a patient H who lies on a bed 17, for example. The carriage 16 has a pair of right and left front wheels 18 and a pair of right and left rear wheels 19. The mobile radiation generation apparatus 10 is movable inside a hospital by the carriage 16. The mobile radiation generation apparatus 10 is used in so-called round imaging for imaging the patient H while visiting patient's rooms. For this reason, the mobile radiation generation apparatus 10 is also referred to as a treatment cart. Alternatively, the mobile radiation generation apparatus 10 is also used in imaging in an emergency room. Furthermore, the mobile radiation generation apparatus 10 can also be carried in an operation room and used in the middle of an operation. In addition, the mobile radiation generation apparatus 10 can also be carried in an outdoor disaster site and used in emergency. The patient H is an example of an "imaging target" according to the technique of the present disclosure.

As is well known, the electronic cassette 11 is a radiographic image detection device that is a sensor panel incorporated in a portable housing and is driven by a battery in a wireless manner. As is also well known, the sensor panel has a configuration in which a plurality of pixels that are sensitive to the radiation R or visible light converted from the radiation R to generate signal charge are arranged. The electronic cassette 11 is placed, for example, below the patient H, receives the radiation R emitted from the radiation generation unit 15 and transmitted through the patient H, and outputs a radiographic image 20.

A body portion 25 is mounted on the carriage 16. The body portion 25 includes a center portion 26, a column portion 27, an arm portion 28, and the like in addition to the above-described radiation generation unit 15.

Figure 3:
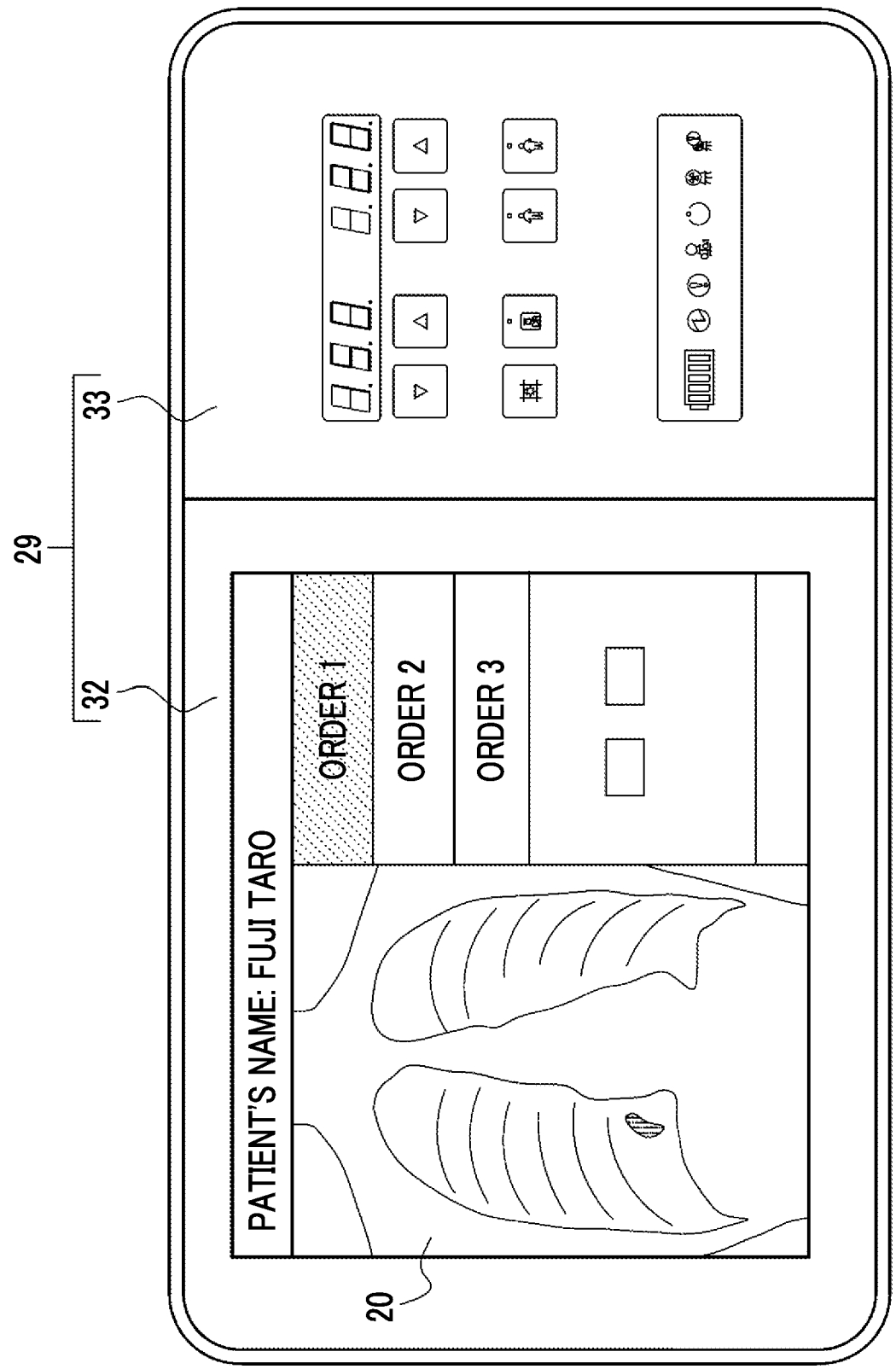
FIG. 3 is a diagram showing a UI-based device.

The center portion 26 has a user interface (UI)-based device 29, a cassette storage portion 30, and a handle 31. The UI-based device 29 is configured of, as shown in FIG. 3, a touch panel display (hereinafter, simply referred to as a display) 32 and an operation panel 33. The display 32 displays the radiographic image 20 and the like. The operation panel 33 is operated by an operator OP, such as a radiographer, in setting irradiation conditions 106 (see FIG. 8) of radiation R. The operator OP is an example of a "person other than an imaging target" according to the technique of the present disclosure.

The cassette storage portion 30 is provided on a rear portion side of the center portion 26. The cassette storage portion 30 stores the electronic cassette 11. There are a plurality of kinds of electronic cassettes 11 having a longitudinal/lateral size of 17 inches 17×inches, 17 inches×14 inches, 12 inches×10 inches, and the like. The cassette storage portion 30 can store a plurality of kinds of electronic cassettes 11 regardless of the kinds. The cassette storage portion 30 has a function of charging a battery of the stored electronic cassette 11.

The handle 31 is provided to surround above the center portion 26. The handle 31 is held by the operator OP to operate not only the carriage 16 but also the mobile radiation generation apparatus 10. The operator OP runs the mobile radiation generation apparatus 10 while holding the handle 31 in a state shown in FIG. 2 in which the radiation generation unit 15 is stored above the carriage 16 and in front of the center portion 26.

An irradiation switch 34 is attached to the center portion 26. The irradiation switch 34 is a switch that is provided to allow the operator OP to give an instruction to start irradiation of radiation. An extension cable is connected to the irradiation switch 34, and can be detached from the center portion 26 for use. The irradiation switch 34 is, for example, a two-stage push switch. The irradiation switch 34 generates a warm-up instruction signal 107 (see FIG. 8) when being pushed to the first stage (half-pushed), and generates an irradiation start instruction signal 108 (see FIG. 8) when being pushed to the second stage (fully pushed).

The column portion 27 has a prismatic columnar shape and is provided upright at the center of the carriage 16. The arm portion 28 has a base end that is attached to the column portion 27, and a distal end that is a free end on an opposite side to the base end and to which the radiation generation unit 15 is attached.

The column portion 27 has a first column 40 and a second column 41 that is consecutively provided upward at a predetermined angle from the first column 40. The first column 40 is provided on an upper surface of the carriage 16. The second column 41 can rotate with respect to the first column 40 with a vertical axis as a rotation axis.

The arm portion 28 can be bent with respect to the second column 41 or can extend in a direction along the second column 41. The radiation generation unit 15 can swing front and back with respect to the arm portion 28.

The radiation generation unit 15 is configured of a radiation source 45, an irradiation field limiter 46, and a camera unit 47. A radiation tube 48 is incorporated in the radiation source 45. The radiation tube 48 generates, for example, X-rays as radiation R. The radiation tube 48 is provided with a filament, a target, a grid electrode, and the like (all are not shown). A voltage from a voltage generator 49 incorporated in the center portion 26 is applied between the filament as a cathode and the target as an anode. The voltage that is applied between the filament and the target is referred to as a tube voltage. The filament discharges thermoelectrons according to the applied tube voltage toward the target. The target radiates radiation R with collision of the thermoelectrons from the filament. The grid electrode is disposed between the filament and the target. The grid electrode changes a flow rate of the thermoelectrons from the filament toward the target according to the voltage applied from the voltage generator 49. The flow rate of the thermoelectrons from the filament toward the target is referred to as a tube current. The tube voltage and the tube current are set as irradiation conditions 106 along with an irradiation time.

In a case where the irradiation switch 34 is half-pushed and the warm-up instruction signal 107 is generated, the filament is warmed up and the rotation of the target is started. When the filament reaches a prescribed temperature, and the target reaches a prescribed rotation speed, warm-up is completed. In a case where the irradiation switch 34 is fully pushed and the irradiation start instruction signal 108 is generated in a state in which the warm-up is completed, the tube voltage is applied from the voltage generator 49, and radiation R is generated from the radiation tube 48. When the irradiation time set in the irradiation conditions 106 has elapsed from the start of generation of radiation R, the application of the tube voltage is stopped, and irradiation of radiation R ends.

The irradiation field limiter 46 limits an irradiation field of radiation R generated from the radiation tube 48. For example, the irradiation field limiter 46 has a configuration in which four shield plates formed of lead or the like shielding radiation R are disposed on respective sides of a quadrangle, and an emission opening of the quadrangle transmitting radiation is formed in a center portion. The irradiation field limiter 46 changes the positions of the shield plates to change the size of the emission opening, and accordingly, changes the irradiation field of radiation R.

The irradiation field limiter 46 has a sensor that detects an opening degree of the emission opening by the shield plates. The irradiation field limiter 46 outputs opening degree information 110 (see FIG. 8) of the emission opening detected by the sensor.

Figure 4:
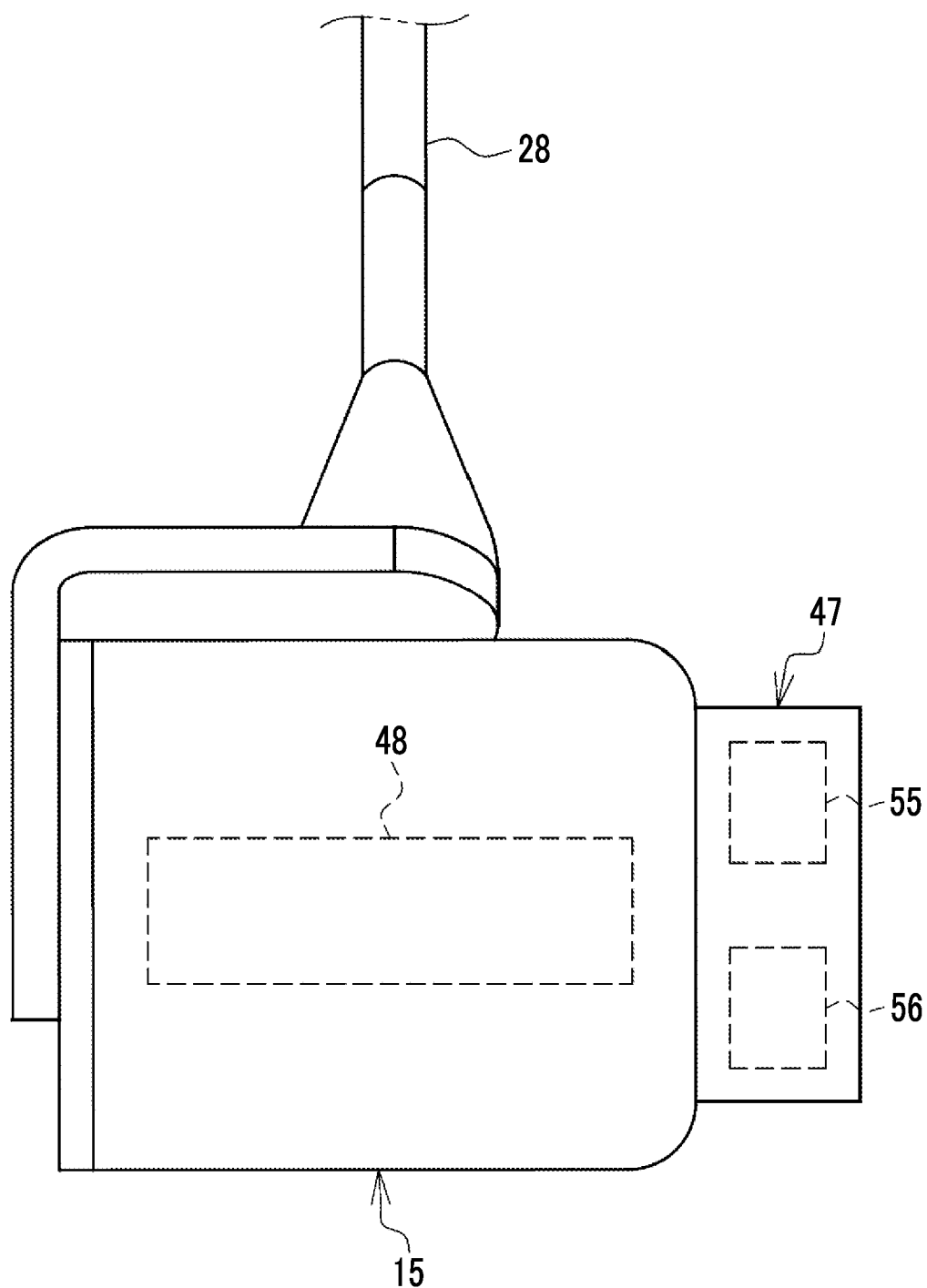
FIG. 4 is a diagram showing a camera unit of a radiation generation unit.

As shown in FIG. 4, a visible light camera 55 and a distance measurement camera (hereinafter, referred to as a time-of-flight (TOF) camera) 56 are incorporated in the camera unit 47. The visible light camera 55 is a camera that literally images visible light. As is well known, the TOF camera 56 is a camera that measures a distance to an object using a time-of-flight method. The visible light camera 55 is an example of a "camera" according to the technique of the present disclosure. The TOF camera 56 is an example of a "distance sensor" according to the technique of the present disclosure.

Not only the camera unit 47 but also the visible light camera 55 and the TOF camera 56 are provided in the radiation generation unit 15 including the radiation tube 48. For this reason, the visible light camera 55 and the TOF camera 56 are supposed to be at the same position as the radiation tube 48 (a generation point of radiation R) when viewed from the patient H side. Furthermore, even though the position of the radiation generation unit 15 is moved due to front-back swing or the like, the visible light camera 55 and the TOF camera 56, and the radiation tube 48 are constantly in the same positional relationship. Similarly, the visible light camera 55 and the TOF camera 56, and the irradiation field limiter 46 are constantly in the same positional relationship.

Figure 5:
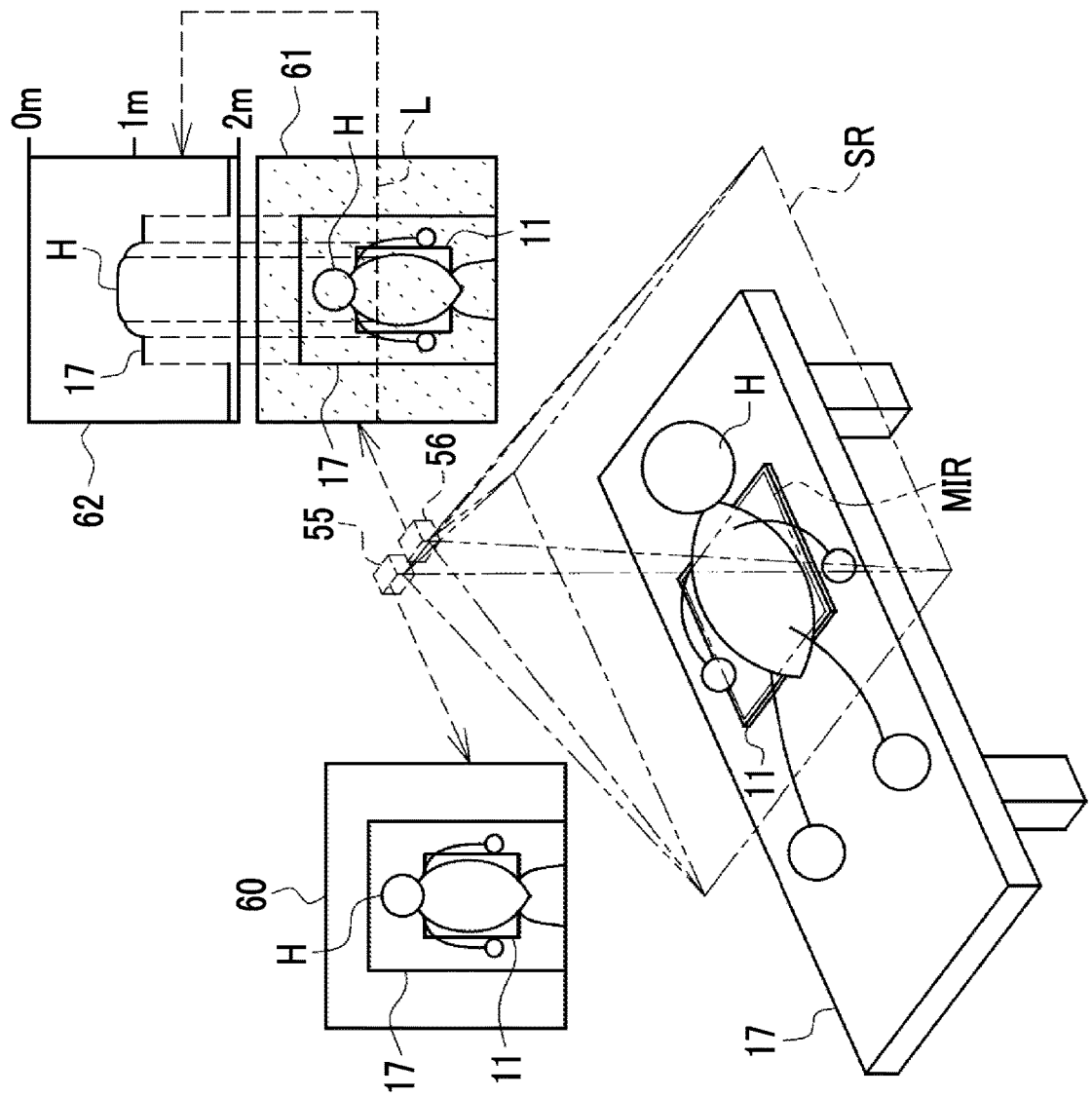
FIG. 5 is a diagram showing a manner in which a patient and a periphery of the patient are imaged with a visible light camera to output a color image and a distance image indicating a distance between a radiation tube and an object is detected with a TOF camera and is output.

As shown in FIG. 5, the visible light camera 55 images a rectangular imaging range SR including the patient H and the periphery of the patient H and outputs a color image 60. The imaging range SR is a range sufficiently wider than a maximum irradiation range MIR of radiation R. The color image 60 is an example of an "optical image" according to the technique of the present disclosure.

The TOF camera 56 images the same imaging range SR as the visible light camera 55 and detects and outputs a distance image 61 indicating a distance from the radiation tube 48 to the object. The distance image 61 is an image that has a distance of an object in the imaging range SR, such as the patient H or the bed 17, as a pixel value of each pixel with the position of the radiation tube 48 represented as 0 m as illustrated by a profile 62 of a line L at the center. The distance image 61 is an example of a "distance information" according to the technique of the present disclosure.

Figure 6:
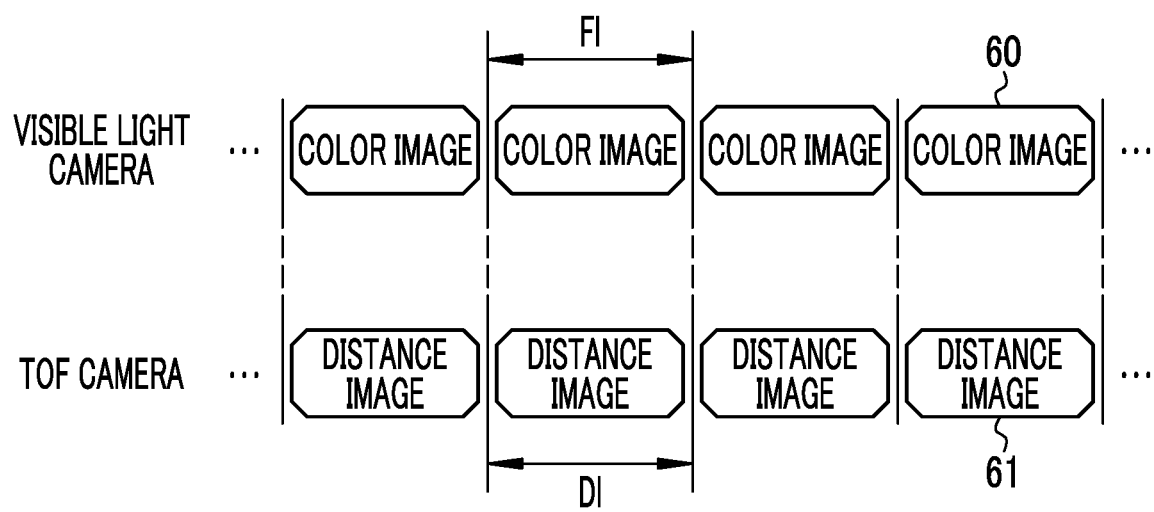
FIG. 6 is a diagram showing a frame interval of the color image and a detection interval of the distance image.

As shown in FIG. 6, the visible light camera 55 sequentially outputs the color image 60 in compliance with a preset frame interval FI. The TOF camera 56 sequentially detects and outputs the distance image 61 in compliance with a detection interval DI according to the frame interval FI, in this case, the detection interval DI equal to the frame interval FI. The frame interval FI is, for example, about 0.0167 seconds (when converted into a frame rate, 60 fps (frames per second)). The detection interval DI may not be equal to the frame interval FI or may be, for example, ten times the frame interval FI.

Figure 7:
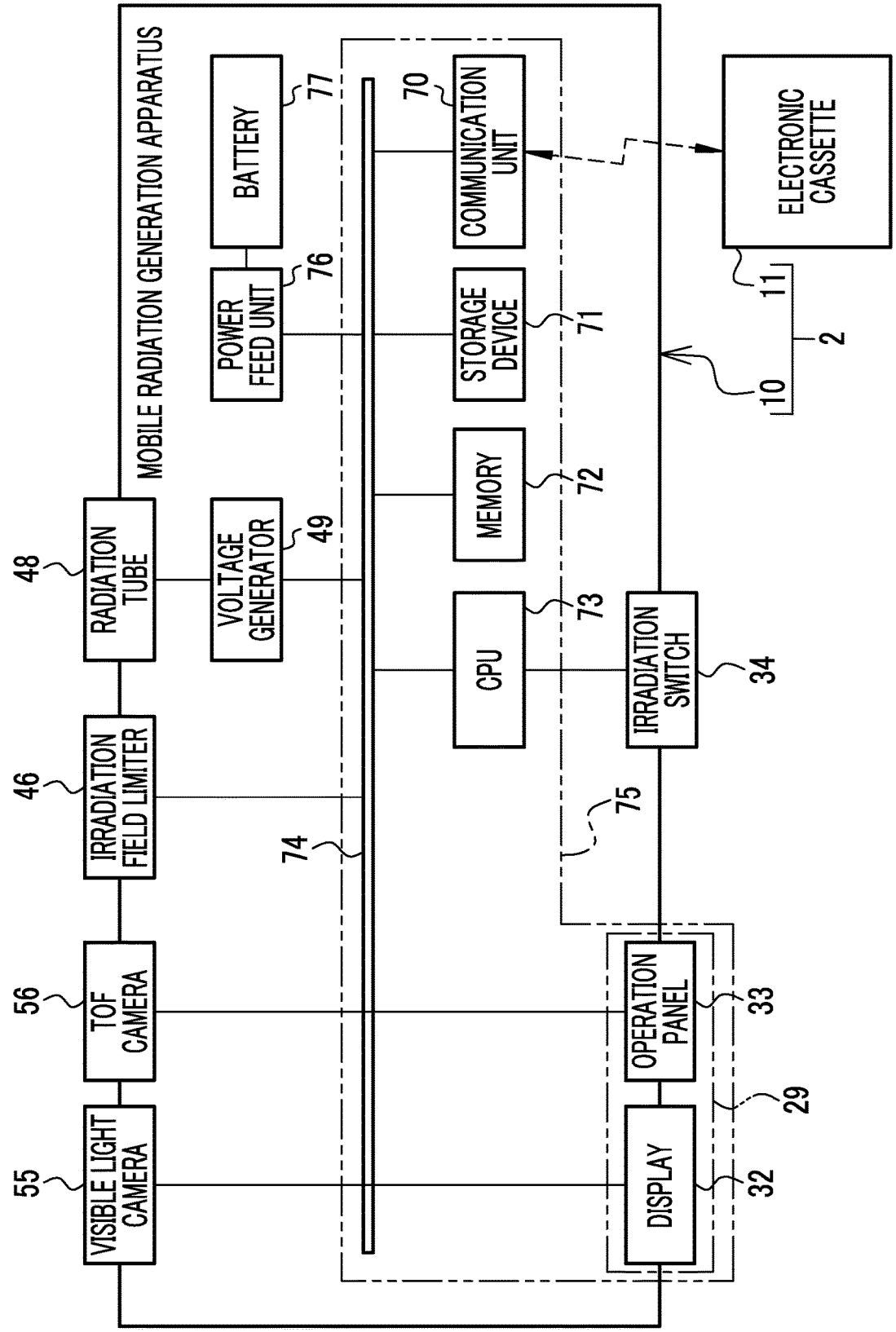
FIG. 7 is a block diagram of a mobile radiation generation apparatus.

In FIG. 7, the mobile radiation generation apparatus 10 has a communication unit 70, a storage device 71, a memory 72, a central processing unit (CPU) 73, and the like. The communication unit 70, the storage device 71, the memory 72, the CPU 73, and the like are connected to one another through a busline 74. The UI-based device 29, the irradiation field limiter 46, the voltage generator 49, the visible light camera 55, and the TOF camera 56 are also connected to the busline 74. The communication unit 70, the storage device 71, the memory 72, the CPU 73, and the busline 74, and the UI-based device 29 configure a console 75. The console 75 is an example of a "radiation intensity estimation apparatus" according to the technique of the present disclosure. The storage device 71, the memory 72, the CPU 73, and the busline 74 are an example of a "computer" according to the technique of the present disclosure. The CPU 73 is an example of a "processor" according to the technique of the present disclosure.

The communication unit 70 includes a wireless communication interface that performs wireless communication with the electronic cassette 11. The communication unit 70 includes a network interface that performs wireless communication with an external device other than the electronic cassette 11 through a network. Examples of the external device include a radiology information system (RIS) that manages information, such as an imaging order and picture archiving and communication systems (PACS). Examples of the network include a wide area network (WAN), such as the Internet or a public communication network.

The storage device 71 is, for example, a hard disk drive or a solid state drive, and stores various programs and various kinds of data associated with various programs. The memory 72 is a work memory on which the CPU 73 executes processing. The CPU 73 reads a program stored in the storage device 71 to the memory 72 and executes processing compliant with the read program. With this, the CPU 73 integrally controls the operations of the units of the mobile radiation generation apparatus 10.

The above-described irradiation switch 34 is connected to the CPU 73. The irradiation switch 34 outputs the warm-up instruction signal 107 and the irradiation start instruction signal 108 to the CPU 73.

A power feed unit 76 is connected to the busline 74. The power feed unit 76 supplies electric power from a battery 77 to the units of the mobile radiation generation apparatus 10. The power feed unit 76 includes a direct-current (DC)-DC converter that converts a direct-current voltage from the battery 77 to a voltage having a value according to a supply destination, a voltage stabilization circuit that stabilizes the value of the converted voltage, and the like. The battery 77 is incorporated in, for example, the center portion 26. In this way, the mobile radiation generation apparatus 10 is driven by the battery 77 in a wireless manner. The mobile radiation generation apparatus 10 can connect a plug (not shown) of a power cord to a socket of a commercial power supply extending from a lower portion of the body portion 25 to charge the battery 77 or can operate with electric power from the commercial power supply.

Figure 8:
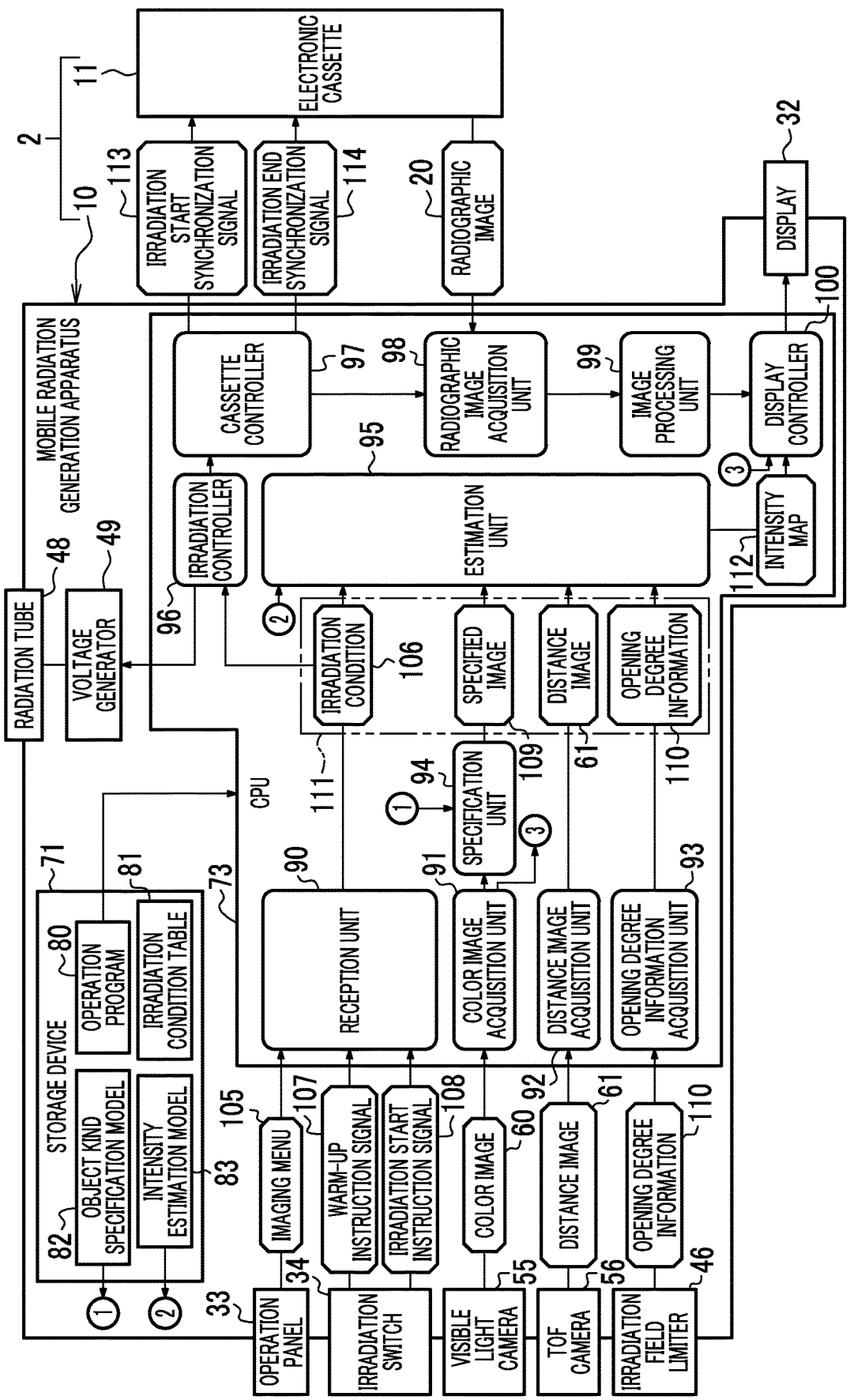
FIG. 8 is a block diagram showing functions of a CPU of a console.

In FIG. 8, an operation program 80 is stored in the storage device 71. The operation program 80 is a program that causes a computer configured of the storage device 71, the memory 72, the CPU 73, and the busline 74 to operate as a "radiation intensity estimation apparatus" according to the technique of the present disclosure. That is, the operation program 80 is an example of an "operation program for a radiation intensity estimation apparatus" according to the technique of the present disclosure. In the storage device 71, an irradiation condition table 81, an object kind specification model 82, and an intensity estimation model 83 are also stored.

The CPU 73 executes the operation program 80 to function as a reception unit 90, a color image acquisition unit 91, a distance image acquisition unit 92, an opening degree information acquisition unit 93, a specification unit 94, an estimation unit 95, an irradiation controller 96, a cassette controller 97, a radiographic image acquisition unit 98, an image processing unit 99, and a display controller 100 in cooperation with the memory 72 and the like.

The reception unit 90 receives an imaging menu 105 input from the operator OP through the operation panel 33. The reception unit 90 reads the irradiation conditions 106 corresponding to the received imaging menu 105 from the irradiation condition table 81 and outputs the read irradiation conditions 106 to the estimation unit 95 and the irradiation controller 96.

The reception unit 90 also receives the warm-up instruction signal 107 and the irradiation start instruction signal 108 from the irradiation switch 34. The reception unit 90 outputs the reception of the warm-up instruction signal 107 and the reception of the irradiation start instruction signal 108 to the irradiation controller 96.

The color image acquisition unit 91 acquires the color image 60 from the visible light camera 55. That is, the color image acquisition unit 91 is an example of an "optical image acquisition unit" that executes "optical image acquisition processing" according to the technique of the present disclosure. The color image acquisition unit 91 starts the acquisition of the color image 60 when the imaging menu 105 is received in the reception unit 90. The color image acquisition unit 91 outputs the color image 60 to the specification unit 94 and the display controller 100.

The distance image acquisition unit 92 acquires the distance image 61 from the TOF camera 56. That is, the distance image acquisition unit 92 is an example of a "distance information acquisition unit" that executes "distance information acquisition processing" according to the technique of the present disclosure. Like the color image acquisition unit 91, the distance image acquisition unit 92 starts the acquisition of the distance image 61 when the imaging menu 105 is received in the reception unit 90. The distance image acquisition unit 92 outputs the distance image 61 to the estimation unit 95.

The opening degree information acquisition unit 93 acquires the opening degree information 110 from the irradiation field limiter 46. Like the color image acquisition unit 91 and the distance image acquisition unit 92, the opening degree information acquisition unit 93 starts the acquisition of the opening degree information 110 when the imaging menu 105 is received in the reception unit 90. The opening degree information acquisition unit 93 outputs the opening degree information 110 to the estimation unit 95.

The specification unit 94 specifies a kind of an object in the color image 60. That is, the specification unit 94 is an example of a "specification unit" that executes "specification processing" according to the technique of the present disclosure. The specification unit 94 outputs a specification image 109 (also see FIG. 11) as a specification result of the kind of the object to the estimation unit 95.

The distance image 61, the irradiation condition 106, the specification image 109, and the opening degree information 110 configure reference information 111. The estimation unit 95 estimates an intensity of radiation R in an environment captured in the color image 60 based on the reference information 111 before radiography. That is, the estimation unit 95 is an example of an "estimation unit" that executes "estimation processing" according to the technique of the present disclosure. The estimation unit 95 outputs an intensity map 112 (also see FIG. 14) as an estimation result of the intensity of radiation R to the display controller 100.

The irradiation controller 96 controls the operation of the radiation tube 48 to control irradiation of radiation R. The irradiation controller 96 sets the irradiation conditions 106 in the voltage generator 49. The irradiation controller 96 makes the radiation tube 48 perform warm-up in a case where the reception of the warm-up instruction signal 107 is input from the reception unit 90. Furthermore, the irradiation controller 96 causes the irradiation of the radiation R from the radiation tube 48 through the voltage generator 49 under the set irradiation conditions 106 in a case where the reception of the irradiation start instruction signal 108 is input from the reception unit 90.

The irradiation controller 96 outputs the start of the irradiation of the radiation R to the cassette controller 97 in conformity with an irradiation start timing of the radiation R. Furthermore, the irradiation controller 96 outputs the end of the irradiation of the radiation R to the cassette controller 97 in conformity with an irradiation end timing of the radiation R.

The cassette controller 97 transmits various control signals to the electronic cassette 11 through the communication unit 70 to control the operation of the electronic cassette 11. The cassette controller 97 transmits an irradiation start synchronization signal 113 to the electronic cassette 11 in a case where the start of the irradiation of the radiation R is input from the irradiation controller 96. Furthermore, the cassette controller 97 transmits an irradiation end synchronization signal 114 to the electronic cassette 11 in a case where the end of the irradiation of the radiation R is input from the irradiation controller 96. Though not shown, the cassette controller 97 transmits a gain value and the like of signal charge according to the irradiation conditions 106 to the electronic cassette 11.

The radiographic image acquisition unit 98 acquires the radiographic image 20 from the electronic cassette 11. The radiographic image acquisition unit 98 outputs the radiographic image 20 to the image processing unit 99.

The image processing unit 99 executes image processing on the radiographic image 20. Specifically, the image processing unit 99 executes offset correction processing, sensitivity correction processing, defective pixel correction processing, and the like as the image processing. The offset correction processing is processing of subtracting, from the radiographic image 20, an offset correction image detected in a state in which there is no irradiation of the radiation R, in units of pixels. The image processing unit 99 executes the offset correction processing to remove fixed pattern noise due to dark charge or the like from the radiographic image 20. The sensitivity correction processing is processing of correcting variation or the like in sensitivity of each pixel, variation in output characteristic of a circuit that reads the signal charge, and the like based on sensitivity correction data. The defective pixel correction processing is processing of linearly interpolating a pixel value of a defective pixel with a pixel value of a surrounding normal pixel based on information of a defective pixel having an abnormal pixel value generated during shipment, during a periodic inspection, or the like. The offset correction processing, the sensitivity correction processing, and the defective pixel correction processing are processing essential for making the image quality of the radiographic image 20 enough to endure display. The image processing unit 99 outputs the radiographic image 20 subjected to various kinds of image processing to the display controller 100.

As shown in FIG. 3, the display controller 100 performs control such that the radiographic image 20 is displayed on the display 32. Furthermore, the display controller 100 performs control such that the intensity map 112 is displayed on the display 32 (see FIG. 17).

Figures 9, 10:
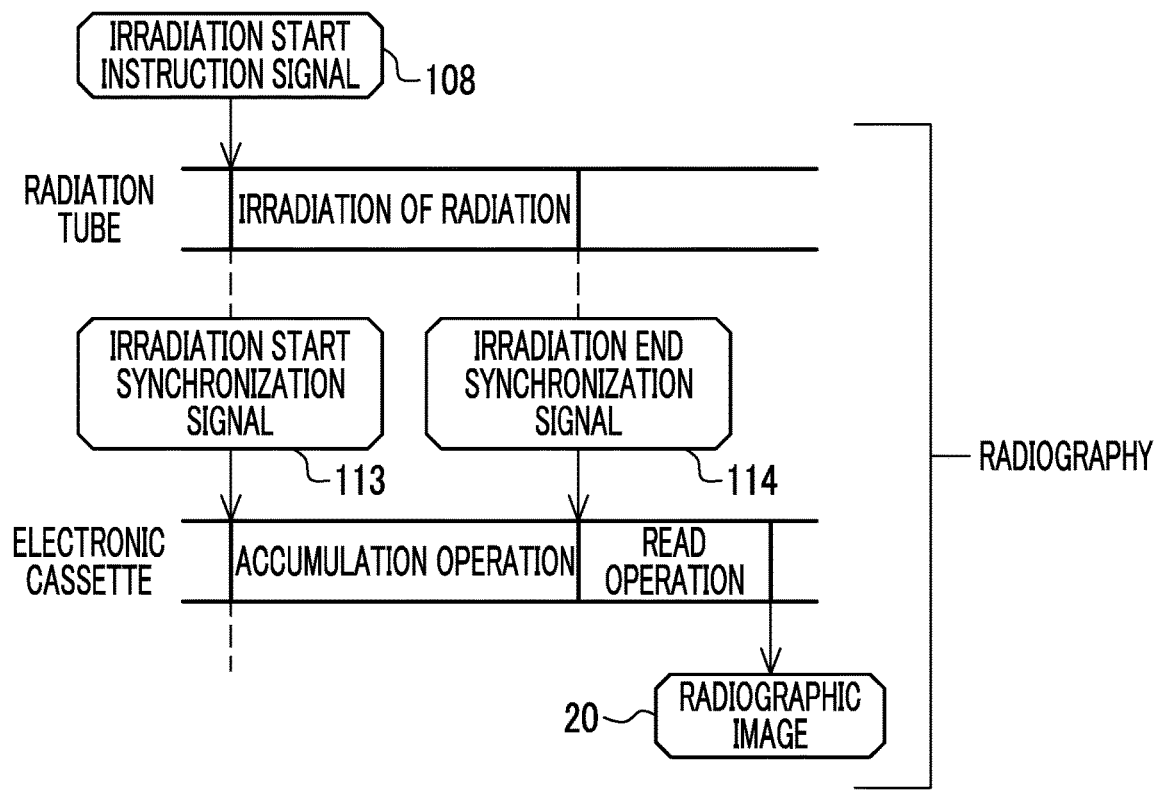
FIG. 9 is a diagram showing an irradiation condition table.
FIG. 10 is a diagram showing radiography.

As shown in FIG. 9, in the irradiation condition table 81, the irradiation conditions 106 corresponding to various imaging menus 105 are registered. The imaging menu 105 defines an imaging procedure having a set of an imaging part, a posture, and an imaging direction, such as "front chest decubitus". The imaging part is a head, a neck, an abdomen, a waist, a shoulder, an elbow, a hand, a knee, an ankle, and the like in addition to the chest. The posture is an upright posture, a sitting posture, and the like in addition to the decubitus posture. The imaging direction is a rear surface, a lateral surface, and the like in addition to the front surface. Further, information regarding a body shape of the patient H, such as "body shape small", is also included in the imaging menu 105. As described above, the irradiation condition 106 is a set of a tube voltage, a tube current, and an irradiation time. Instead of the tube current and the irradiation time, a tube current and irradiation time product may be set as the irradiation condition 106.

The mobile radiation generation apparatus 10 receives an imaging order from the RIS through the communication unit 70. In the imaging order, identification data (ID) for identifying the patient H, instruction information of an imaging procedure by a treatment department physician or the like who issues an imaging order, and the like are registered. The mobile radiation generation apparatus 10 displays the imaging order from the RIS on the display 32 according to an operation of the operator OP. The operator OP confirms the content of the imaging order through the display 32.

The mobile radiation generation apparatus 10 displays one of a plurality of electronic cassettes 11 stored in the cassette storage portion 30 on the display 32 in a selectable form. The operator OP selects one electronic cassette 11 that is used to image the patient H indicated by the imaging order. With this, the selected electronic cassette 11 and the imaging order are associated with each other.

Furthermore, the mobile radiation generation apparatus 10 displays the imaging menu 105 on the display 32 in a selectable form. The operator OP selects the imaging menu 105 that coincides with the imaging procedure designated by the imaging order and coincides with the body shape of the patient H. With this, the imaging menu 105 is received by the reception unit 90, and the irradiation conditions 106 corresponding to the imaging menu 105 are read from the irradiation condition table 81 to the reception unit 90. As a result, the irradiation conditions 106 are set in the voltage generator 49 by the irradiation controller 96. The irradiation conditions 106 read from the irradiation condition table 81 can be finely adjusted by the operator OP through the operation panel 33 before being set in the voltage generator 49.

As shown in FIG. 10, the radiation tube 48 generates the radiation R in conformity with the irradiation start instruction signal 108 from the irradiation switch 34. The electronic cassette 11 performs an accumulation operation to make the pixels accumulate the signal charge according to the irradiation start synchronization signal 113 transmitted in conformity with the irradiation start timing of the radiation R after performing a reset operation (not shown) to read and discard dark charge from the pixels of the sensor panel. Furthermore, the electronic cassette 11 performs a reading operation to read the signal charge accumulated in the pixels and to output the signal charge as the radiographic image 20 according to the irradiation end synchronization signal 114 transmitted in conformity with the irradiation end timing of the radiation R. A series of operations to cause the irradiation of the radiation R from the radiation tube 48 and to output the radiographic image 20 from the electronic cassette 11 is defined as "radiography" according to the technique of the present disclosure.

Figure 11:
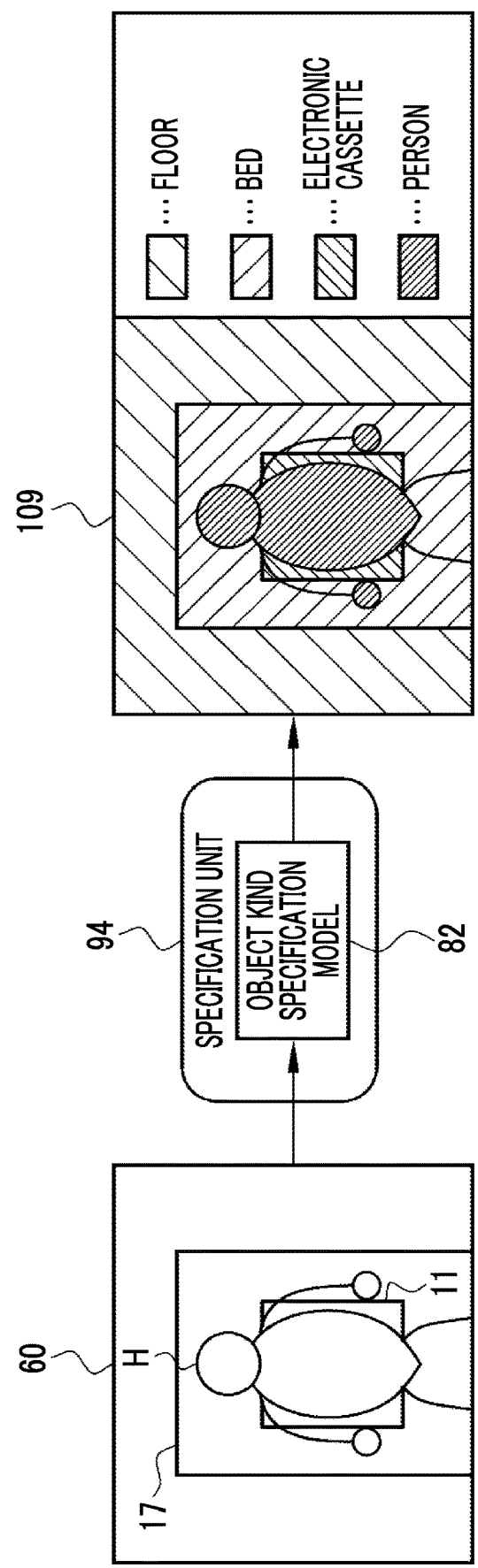
FIG. 11 is a diagram showing a manner in which a kind of the object in the color image is specified using an object kind specification model.

As shown in FIG. 11, the specification unit 94 specifies a kind of an object in the color image 60 using the object kind specification model 82. The object kind specification model 82 is a model where the color image 60 is input data and the specification image 109 that is the specification result of the kind of the object is output data. That is, the object kind specification model 82 is an example of a "first machine learning model" according to the technique of the present disclosure.

The specification image 109 is an image where the kind of the object, a floor, the electronic cassette 11, the bed 17, or a person (patient H), in the color image 60 is discriminated in units of pixels as distinctively indicated by hatching. A method of discriminating the kind of the object in the image in units of pixels is referred to as semantic segmentation. Examples of a machine learning model that performs the semantic segmentation include a U-shaped convolutional neural network (U-Net).

Figure 12:
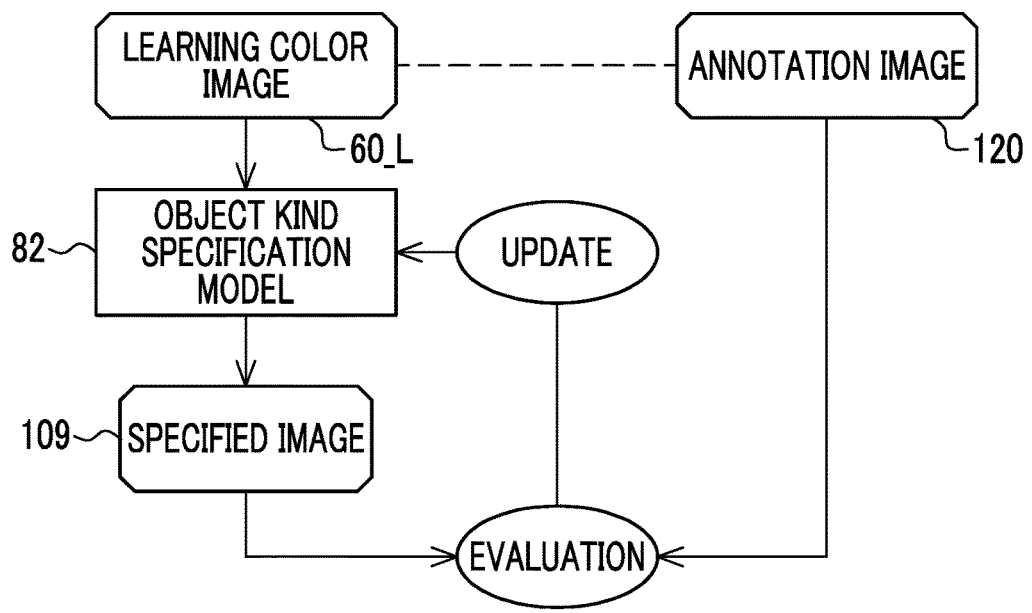
FIG. 12 is a diagram showing a learning phase of the object kind specification model.

As shown in FIG. 12, in a learning phase of the object kind specification model 82, a set of a color image 60_L for learning and an annotation image 120 is used. In the color image 60_L for learning, a plurality of color images 60 in which the patient H and the periphery of the patient H are captured at various imaging places where radiography can be performed with the mobile radiation generation apparatus 10, such as a patient's room, an emergency room, an operation room, and a disaster site, are included. In the color image 60_L for learning, images in which various objects including furniture of the patient's room, such as a chair and a television rack, medical equipment, such as a heart rate meter, an ultrasound diagnostic apparatus, and a defibrillator, medical utensils, such as a drip stand and a hoisting accessory, and persons, such as the operator OP, other medical workers, and an attendant of the patient H, are captured in addition to the floor, the electronic cassette 11, the bed 17, and the person (patient H) illustrated in FIG. 11 are prepared.

The annotation image 120 is an image in which the kind of the object of the color image 60_L for learning is designated in advance, for example, manually. The annotation image 120 is an image for, so to speak, checking answers to the specification image 109 input from the object kind specification model 82 according to the color image 60_L for learning, and is compared with the specification image 109. The higher the discrimination accuracy of the kind of the object of the object kind specification model 82, the higher a probability that the higher annotation image 120 coincides with the specification image 109.

In the learning phase of the object kind specification model 82, the color image 60_L for learning is given as input data to the object kind specification model 82. With this, the specification image 109 is output from the object kind specification model 82. The specification image 109 output from the object kind specification model 82 in this manner is compared with the annotation image 120, and the discrimination accuracy of the kind of the object of the object kind specification model 82 is evaluated. Then, the object kind specification model 82 is updated according to an evaluation result.

In the learning phase, the input of the color image 60_L for learning to the object kind specification model 82, the output of the specification image 109 from the object kind specification model 82, the evaluation of the discrimination accuracy of the kind of the object of the object kind specification model 82, and the update of the object kind specification model 82 are performed while changing a set of the color image 60_L for learning and the annotation image 120 and are repeated until the discrimination accuracy of the kind of the object of the object kind specification model 82 reaches a desired level. The object kind specification model 82 of which the discrimination accuracy of the kind of the object is increased to the desired level is stored in the storage device 71 and is offered to the specification unit 94. The learning phase may be executed even after the storage in the storage device 71 to increase the level of the discrimination accuracy of the kind of the object of the object kind specification model 82.

Figure 13:
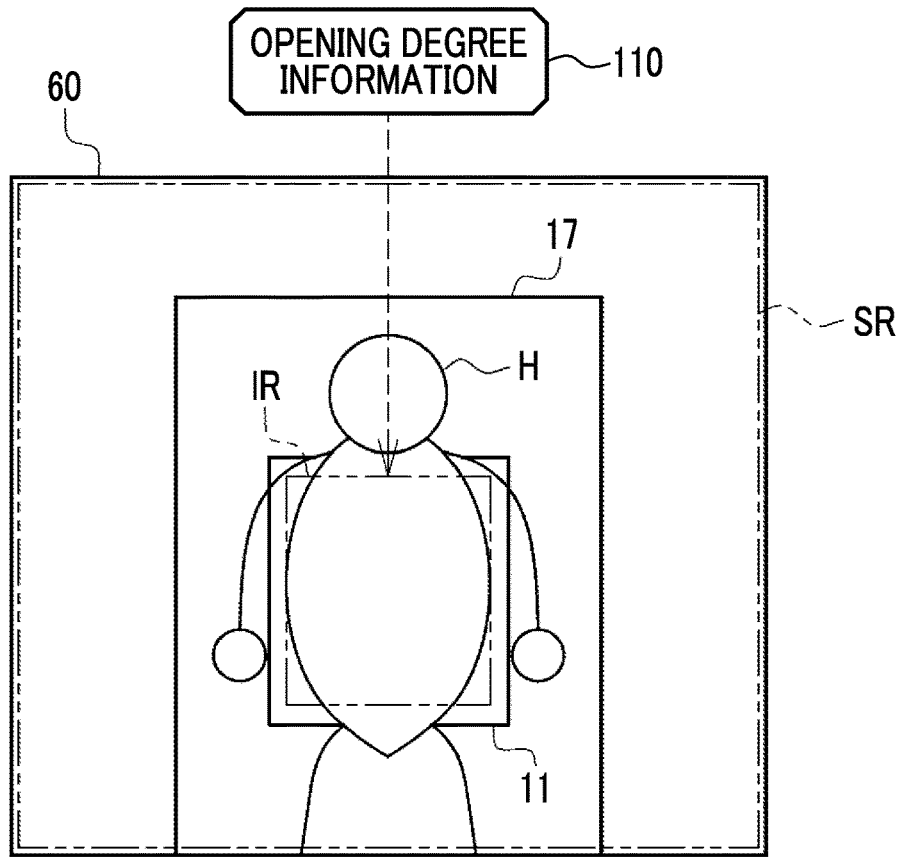
FIG. 13 is a diagram showing a manner in which an irradiation range of radiation is derived from opening degree information.

As described above, the visible light camera 55 and the TOF camera 56, and the irradiation field limiter 46 are constantly in the same positional relationship. For example, as shown in FIG. 13, an irradiation range IR of the radiation R in the environment (imaging range SR) captured in the color image 60 is derived by the opening degree information 110 acquired from the irradiation field limiter 46 in the opening degree information acquisition unit 93.

Figure 14:
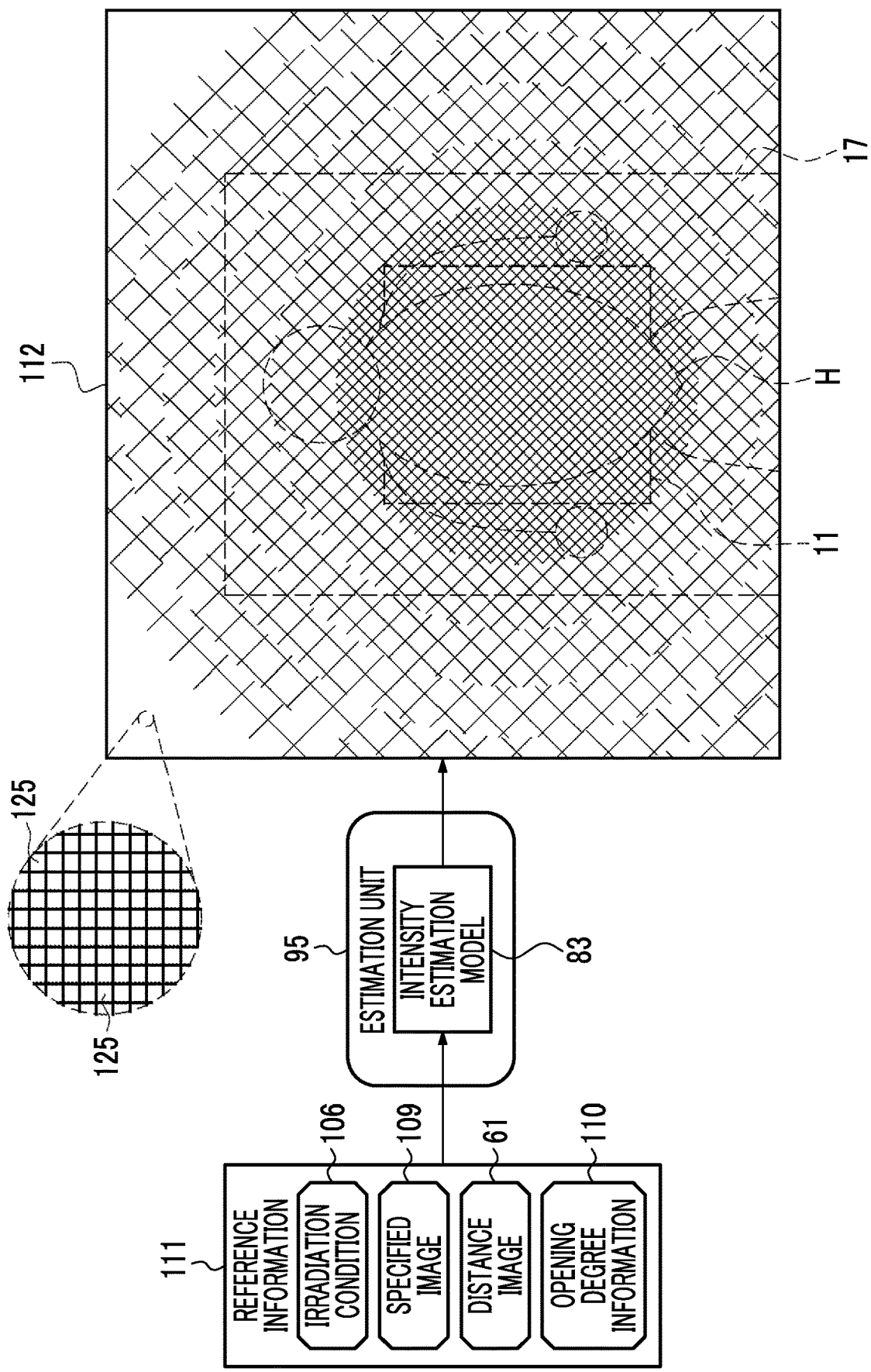
FIG. 14 is a diagram showing a manner in which an intensity of radiation in an environment captured in the color image is estimated using an intensity estimation model.

As shown in FIG. 14, the estimation unit 95 estimates the intensity of the radiation R in the environment captured in the color image 60 using the intensity estimation model 83. The intensity estimation model 83 is a model where the reference information 111 is input data and the intensity map 112 as an estimation result of the intensity is output data. That is, the intensity estimation model 83 is an example of a "second machine learning model" according to the technique of the present disclosure.

The intensity map 112 indicates the level of the intensity of the radiation R of each divided region 125 obtained by equally dividing the color image 60. The divided regions 125 are, for example, the regions by equally dividing the color image 60 into 100×100=10000 regions. In the intensity map 112, the level of the intensity of the radiation R is expressed by a difference in color as indicated by hatching. For example, red to orange are assigned to the divided regions 125 having comparatively high intensity, yellow to green are assigned to the divided regions 125 having a medium degree of intensity, and sky blue to blue are assigned to the divided regions 125 having comparatively low intensity. The unit of the intensity is, for example, milligray (mGy).

Figure 15:
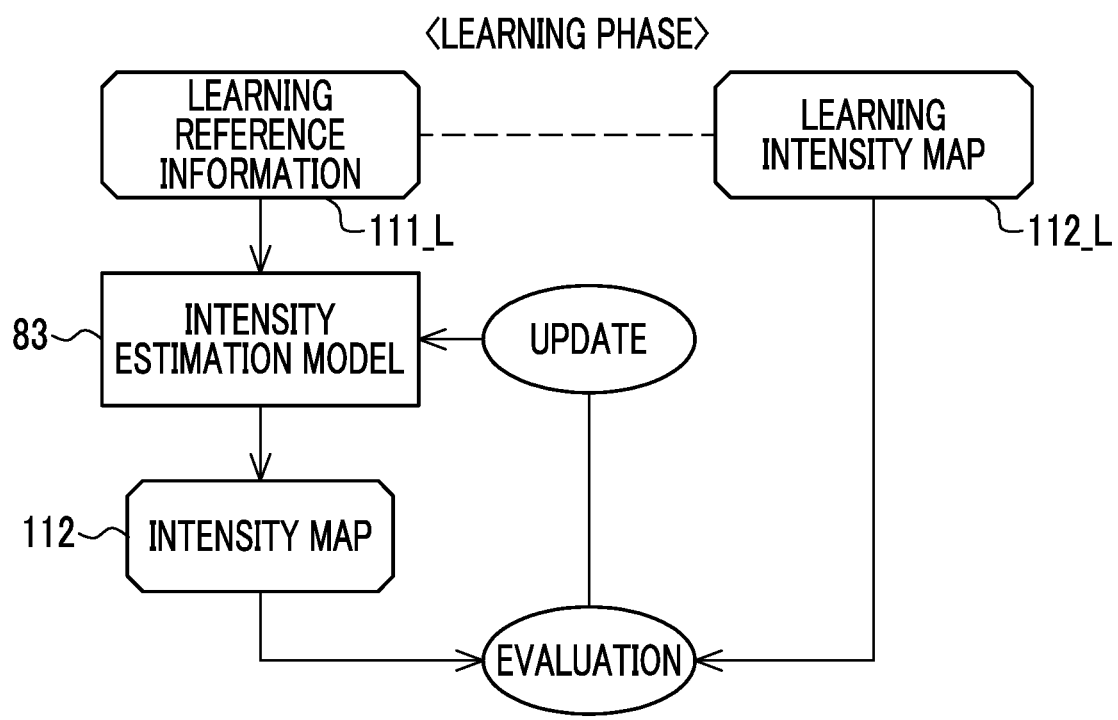
FIG. 15 is a diagram showing a learning phase of the intensity estimation model.

As shown in FIG. 15, in a learning phase of the intensity estimation model 83, a set of reference information 111_L for learning and an intensity map 112_L for learning is used. In the reference information 111_L for learning, various sets of the distance image 61, the irradiation condition 106, the specification image 109, and the opening degree information 110 are prepared.

The intensity map 112_L for learning is an intensity map that is created by measuring the intensity of the radiation R in the reference information 111_L for learning for each divided region 125 with an intensity sensor, for example. The intensity map 112_L for learning is for, so to speak, checking answers to the intensity map 112 output from the intensity estimation model 83 according to the reference information 111_L for learning, and is compared with the intensity map 112. The higher the estimation accuracy of the intensity of the intensity estimation model 83, the higher a probability that the intensity map 112_L for learning coincides with the intensity map 112.

In the learning phase of the intensity estimation model 83, the reference information 111_L for learning is given as input data to the intensity estimation model 83. With this, the intensity map 112 is output from the intensity estimation model 83. The intensity map 112 output from the intensity estimation model 83 in this manner is compared with the intensity map 112_L for learning, and the estimation accuracy of the intensity of the intensity estimation model 83 is evaluated. Then, the intensity estimation model 83 is updated according to an evaluation result.

In the learning phase, the input of the reference information 111_L for learning to the intensity estimation model 83, the output of the intensity map 112 from the intensity estimation model 83, the evaluation of the estimation accuracy of the intensity of the intensity estimation model 83, and the update of the intensity estimation model 83 are performed while changing a set of the reference information 111_L for learning and the intensity map 112_L for learning and are repeated until the estimation accuracy of the intensity of the intensity estimation model 83 reaches a desired level. The intensity estimation model 83 of which the estimation accuracy of the intensity is increased to the desired level is stored in the storage device 71 and is offered to the estimation unit 95. The learning phase may be executed even after the storage in the storage device 71 to increase the level of the estimation accuracy of the intensity of the intensity estimation model 83.

Figure 16:
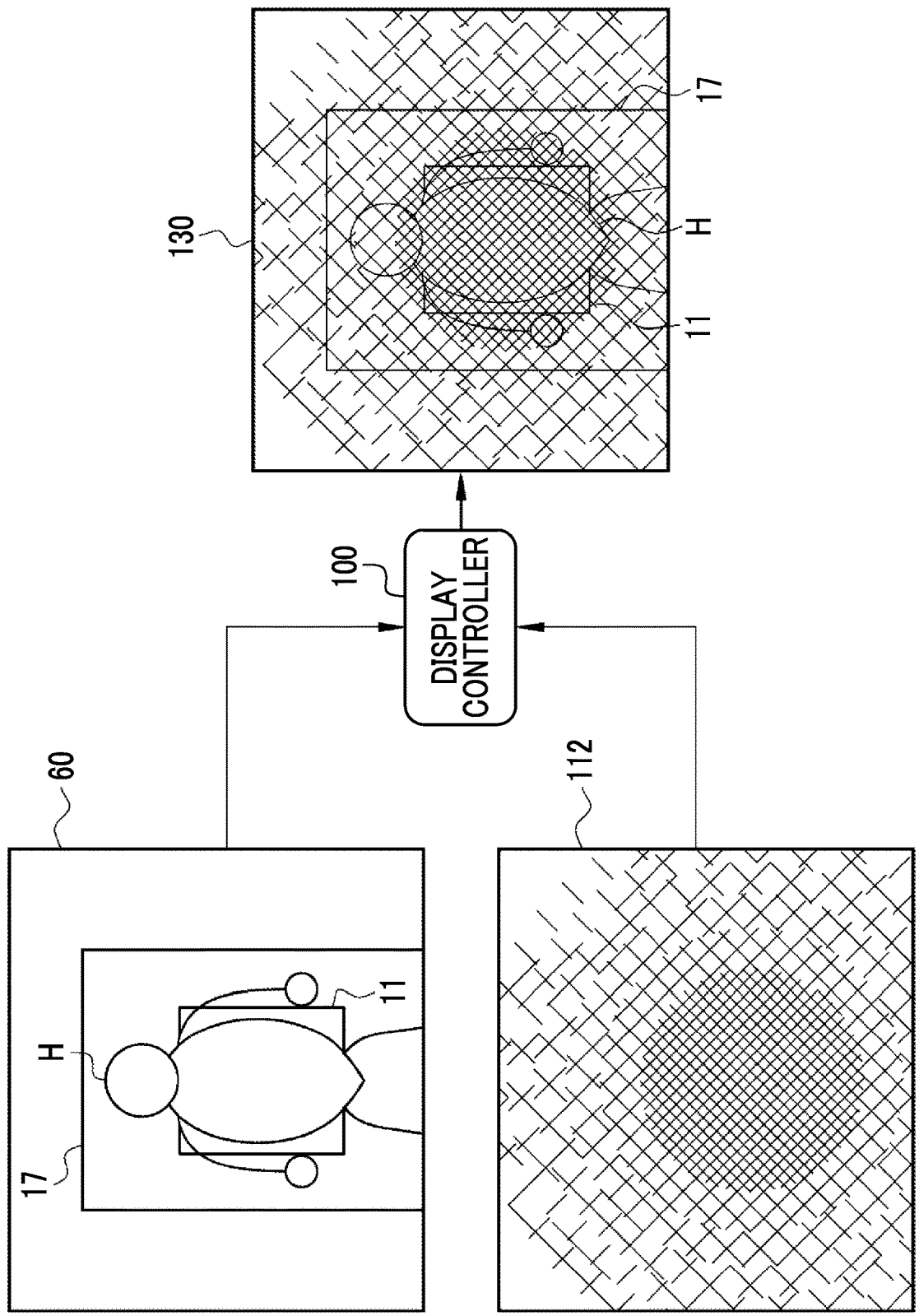
FIG. 16 is a diagram showing a manner in which a superimposed image of the color image and an intensity map is generated.
Figure 17:
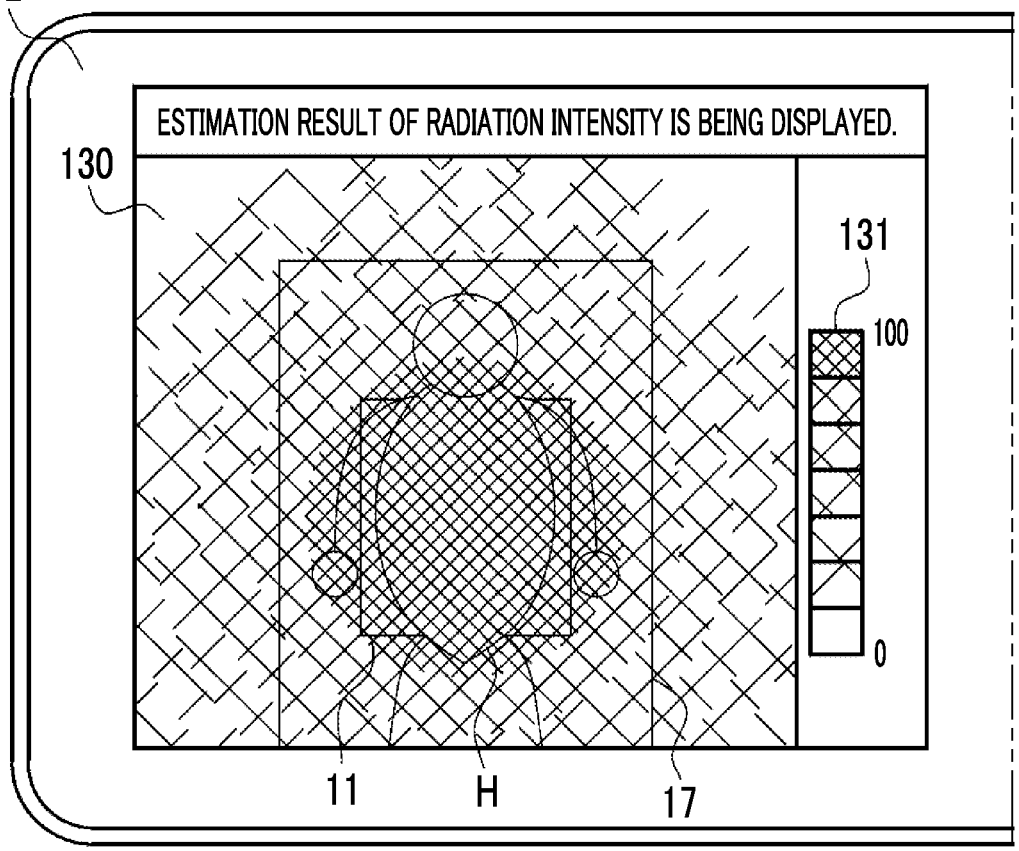
FIG. 17 is a diagram showing a manner in which the superimposed image is displayed on a display.

As shown in FIG. 16, the display controller 100 superimposes the intensity map 112 on the color image 60 to generate a superimposed image 130. As shown in FIG. 17, the display controller 100 displays the superimposed image 130 on the display 32. The display controller 100 displays a color bar 131 indicating a correspondence relationship of the color assigned to the divided region 125 and the intensity beside the superimposed image 130.

Figure 18:
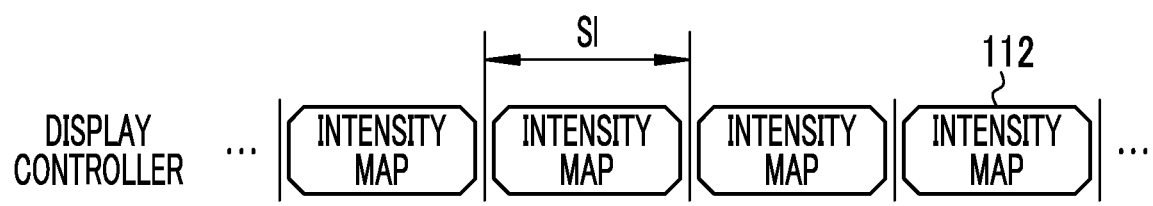
FIG. 18 is a diagram showing a display update interval of the intensity map.
Figure 19:
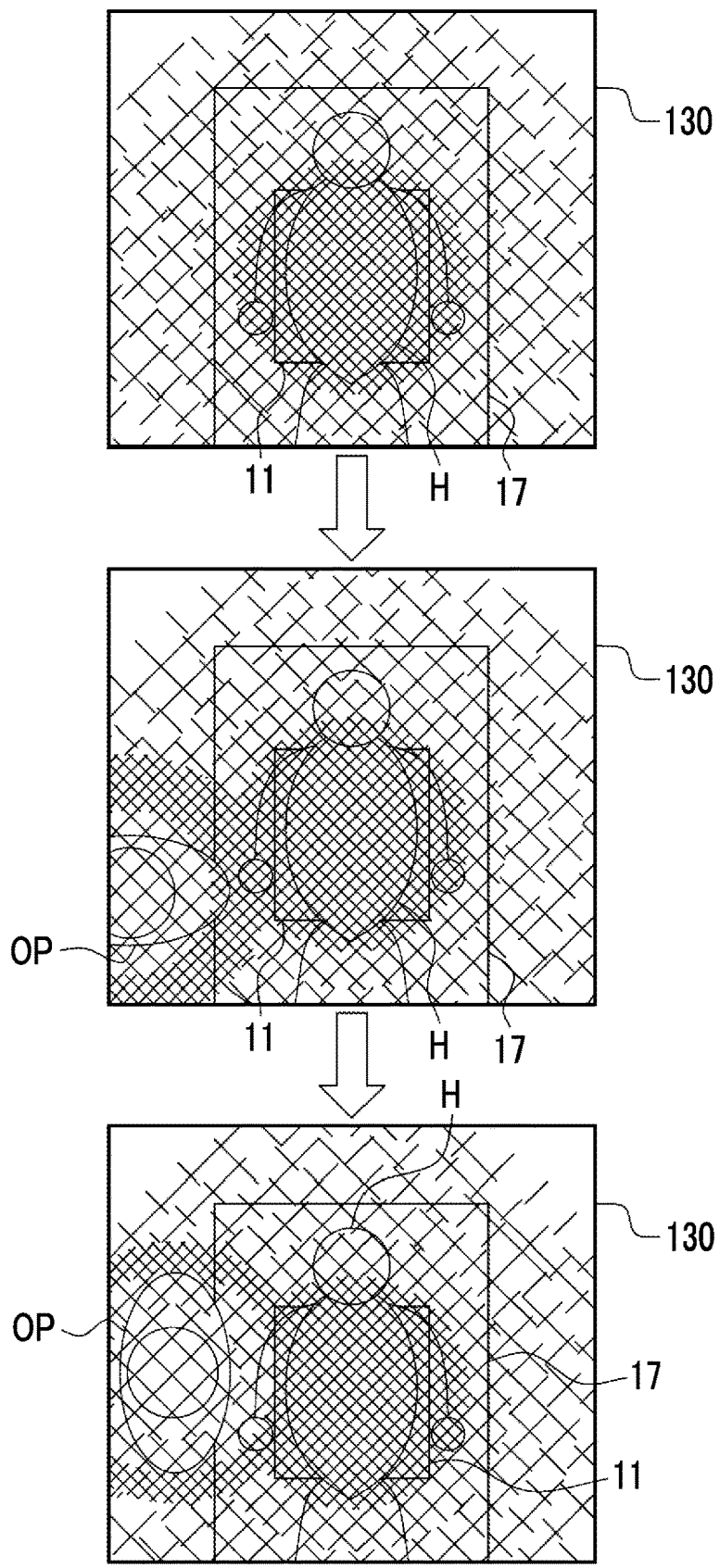
FIG. 19 is a diagram showing transition of the intensity map according to movement of an operator.

As shown in FIG. 18, the display controller 100 updates the display of the intensity map 112 of the superimposed image 130 at a preset time interval SI. The time interval SI is equal to, for example, the frame interval FI of the color image 60. For this reason, as shown in FIG. 19, in a case where the operator OP appears from a right foot side of the patient H and stands on a right chest side of the patient H, the superimposed image 130 in which the intensity map 112 changes every second according to the movement of the operator OP is displayed.

Figure 20:
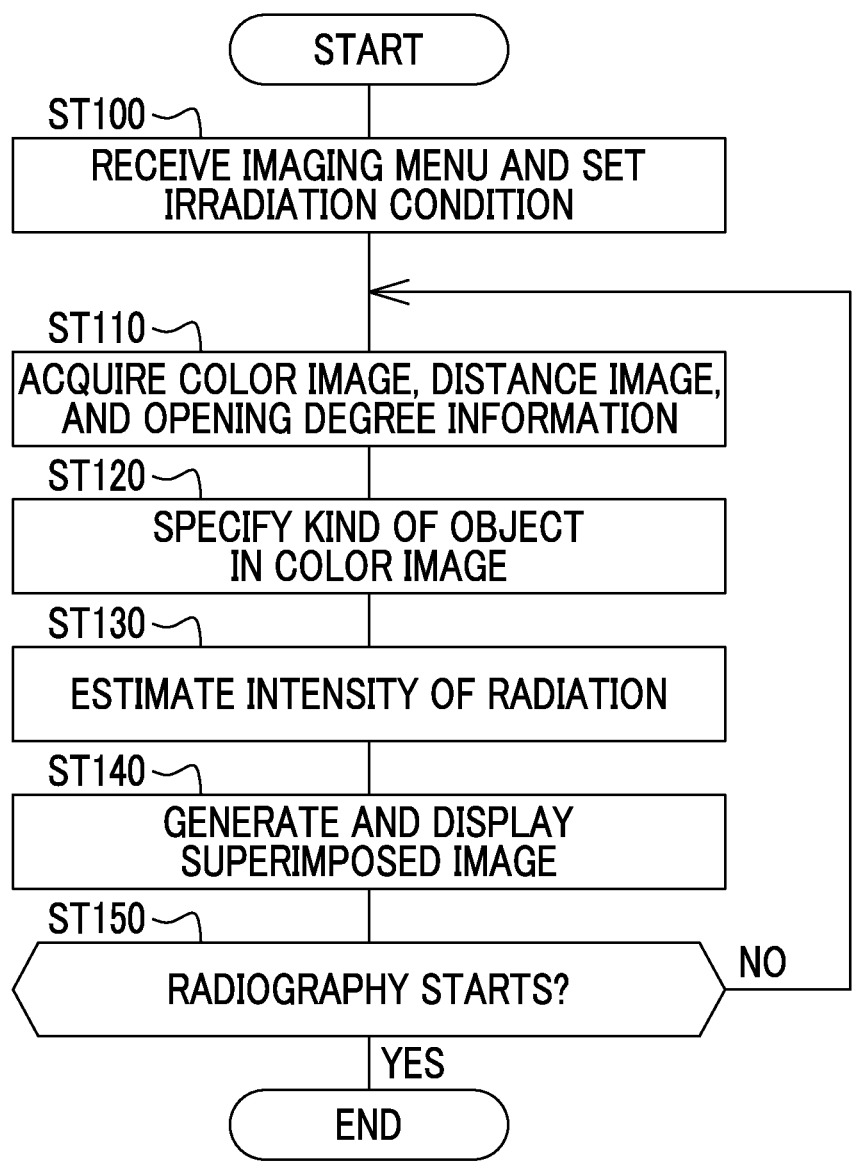
FIG. 20 is a flowchart showing a procedure of radiation intensity estimation.

Next, the operation of the above-described configuration will be described referring to a flowchart of FIG. 20. In a case where the operation program 80 is activated, as shown in FIG. 8, the CPU 73 of the console 75 functions as the reception unit 90, the color image acquisition unit 91, the distance image acquisition unit 92, the opening degree information acquisition unit 93, the specification unit 94, the estimation unit 95, the irradiation controller 96, the cassette controller 97, the radiographic image acquisition unit 98, the image processing unit 99, and the display controller 100.

Before the radiography, the imaging menu 105 corresponding to the imaging order is selected by the operator OP through the display 32, and the imaging menu 105 is received in the reception unit 90. Then, the irradiation conditions 106 corresponding to the imaging menu 105 are read from the irradiation condition table 81 by the reception unit 90. The read irradiation conditions 106 are finely adjusted by the operator OP as needed, and are set in the voltage generator 49 by the irradiation controller 96 (Step ST100). The irradiation condition 106 is also output to the estimation unit 95.

Positioning of the electronic cassette 11, the radiation generation unit 15, and the patient H, adjustment of the opening degree of the emission opening of the irradiation field limiter 46, and the like are performed by the operator OP.

After the irradiation conditions 106 are set, the color image 60 from the visible light camera 55 is acquired in the color image acquisition unit 91. Furthermore, the distance image 61 from the TOF camera 56 is acquired in the distance image acquisition unit 92. As shown in FIG. 6, the color image 60 and the distance image 61 are sequentially output at the frame interval FI and the detection interval DI. In addition, the opening degree information 110 from the irradiation field limiter 46 is acquired in the opening degree information acquisition unit 93 (Step ST110). The color image 60 is output from the color image acquisition unit 91 to the specification unit 94 and the display controller 100. The distance image 61 is output from the distance image acquisition unit 92 to the estimation unit 95. The opening degree information 110 is output from the opening degree information acquisition unit 93 to the estimation unit 95. Step ST110 is an example of an "optical image acquisition step" and a "distance information acquisition step" according to the technique of the present disclosure.

As shown in FIG. 11, the kind of the object in the color image 60 is specified by the specification unit 94 using the object kind specification model 82 (Step ST120). With this, the specification image 109 as the specification result of the kind of the object is output from the object kind specification model 82. The specification image 109 is output from the specification unit 94 to the estimation unit 95. Step ST120 is an example of a "specification step" according to the technique of the present disclosure.

The reference information 111 configured of the distance image 61, the irradiation condition 106, the specification image 109, and the opening degree information 110 is input to the estimation unit 95. Then, as shown in FIG. 14, the intensity of the radiation R in the environment captured in the color image 60 is estimated by the estimation unit 95 using the intensity estimation model 83 (Step ST130). With this, the intensity map 112 as the estimation result of the intensity is output from the intensity estimation model 83. The intensity map 112 is output from the estimation unit 95 to the display controller 100. Step ST130 is an example of an "estimation step" according to the technique of the present disclosure.

As shown in FIG. 16, the superimposed image 130 in which the color image 60 and the intensity map 112 are superimposed is generated by the display controller 100. As shown in FIG. 17, the superimposed image 130 is displayed on the display 32 under the control of the display controller 100 (Step ST140). With this, the superimposed image 130 is offered to an inspection of the operator OP or the like. As shown in FIG. 18, the display of the intensity map 112 of the superimposed image 130 is updated at the time interval SI. The processing of Steps ST110 to ST140 is repeatedly continued until the radiography is started (in Step ST150, YES).

The irradiation switch 34 is operated by the operator OP, and the warm-up instruction signal 107 and the irradiation start instruction signal 108 are received in the reception unit 90. With this, as shown in FIG. 10, the irradiation of the radiation R from the radiation tube 48 is made under the set irradiation conditions 106. Furthermore, in the electronic cassette 11, the accumulation operation is performed according to the irradiation start synchronization signal 113, and the reading operation is performed according to the irradiation end synchronization signal 114. With this, the radiographic image 20 is output from the electronic cassette 11.

The radiographic image 20 is acquired in the radiographic image acquisition unit 98. The radiographic image 20 is output from the radiographic image acquisition unit 98 to the image processing unit 99, is subjected to various kinds of image processing in the image processing unit 99, and is then output to the display controller 100. Then, as shown in FIG. 3, the radiographic image 20 is displayed on the display 32 under the control of the display controller 100.

As described above, the CPU 73 of the console 75 comprises the color image acquisition unit 91, the distance image acquisition unit 92, the specification unit 94, and the estimation unit 95. The color image acquisition unit 91 acquires the color image 60, in which the patient H and the periphery of the patient H are captured, from the visible light camera 55. The distance image acquisition unit 92 acquires the distance image 61 indicating the distance from the radiation tube 48 to the object from the TOF camera 56. The specification unit 94 specifies a kind of an object in the color image 60. The estimation unit 95 estimates the intensity of the radiation R in the environment captured in the color image 60 based on the reference information 111 including the distance image 61 and the specification image 109 as the specification result of the kind of the object. Accordingly, in a case where the mobile radiation generation apparatus 10 is used, even though any object is present in the periphery of the patient H, and information indicating how far the object and the radiation tube 48 are separated is not preset, it is possible to appropriately estimate the intensity of the radiation R according to circumstances in the periphery of the patient H changing depending on the imaging place.

The reference information 111 further includes the irradiation conditions 106 and the opening degree information 110 in addition to the distance image 61 and the specification image 109. For this reason, it is possible to further increase the estimation accuracy of the intensity of the radiation R.

The display controller 100 controls the display of the intensity map 112 as the estimation result of the intensity. For this reason, it is possible to notify the operator OP or the like of the intensity map 112.

The display controller 100 displays the color image 60 and the intensity map 112 together. In more detail, the display controller 100 displays the intensity map 112 on the color image 60 in a superimposed manner. For this reason, it is possible to notify the operator OP or the like of a region where the intensity is high and there is a need to avoid in the imaging range SR of the color image 60. It is possible to allow the operator OP or the like to take behavior for avoiding careless exposure, such as evacuating from a region where the intensity is high.

The display controller 100 displays the intensity map 112 through the display 32 that is mounted in the mobile radiation generation apparatus 10 and displays the radiographic image 20. For this reason, there is no need to prepare a dedicated display unit that displays the intensity map 112, and it is possible to suppress component costs.

The display controller 100 updates the display of the intensity map 112 at the predetermined time interval SI. The mobile radiation generation apparatus 10 is often used at an imaging place where the operator OP and medical workers other than the operator OP frequently come and go, and thus, the circumstance in the periphery of the patient H change every second. Accordingly, in a case where the display of the intensity map 112 is updated at the time interval SI, it is possible to notify the operator OP or the like of the intensity map 112 that changes in real time according to the circumstances in the periphery of the patient H changing every second.

The specification unit 94 uses the object kind specification model 82 where the color image 60 is input data and the specification image 109 as the specification result of the kind of the object is output data. For this reason, it is possible to easily obtain the specification image 109.

The estimation unit 95 uses the intensity estimation model 83 where the reference information 111 is input data and the intensity map 112 as the estimation result of the intensity is output data. For this reason, it is possible to easily obtain the intensity map 112.

The visible light camera 55 and the TOF camera 56 are provided in the radiation generation unit 15 including the radiation tube 48. For this reason, it is possible to derive the irradiation range IR of the radiation R in the environment captured in the color image 60 only with the opening degree information 110.

The visible light camera 55 sequentially outputs the color image 60 in compliance with the preset frame interval FI. The TOF camera 56 sequentially detects and outputs the distance image 61 in compliance with the detection interval DI according to the frame interval FI. For this reason, it is possible to output the intensity map 112 according to the circumstances in the periphery of the patient H changing every second.

The visible light camera 55 is used as a "camera" according to the technique of the present disclosure. For this reason, an object is easily specified.

Furthermore, the TOF camera 56 is used as a "distance sensor" according to the technique of the present disclosure. As the distance sensor, instead of the TOF camera 56, a stereo camera that measures a distance to an object from an image captured with two cameras having parallax, an ultrasound sensor that emits an ultrasonic wave from an ultrasound transducer to measure a distance to an object by an ultrasound echo reflected by the object, or the like may be used. Note that the TOF camera 56 can have a simple device configuration compared to the stereo camera, the ultrasound sensor, or the like, and thus, is more preferably used.

The distance image 61 captured with the TOF camera 56 may be handled as an optical image instead of the color image 60, a kind of an object in the distance image 61 may be specified. This eliminates a need to prepare the visible light camera 55, and makes it possible to configure a "camera" and a "distance sensor" with one TOF camera 56.

In this way, the optical image is not limited to the color image 60. A monochrome image may be handled as an optical image. Note that, in a case where the color image 60 is handled as the optical image, the amount of information is greater than the distance image 61, a monochrome image, or the like to such an extent that there is color information, and thus, it is possible to increase the specification accuracy of the kind of the object.

The size of the divided region 125 is not limited to the size in a case where the color image 60 in the above-described example is equally divided into 10000 regions. A size in units of pixels of the color image 60 may be applied. Furthermore, as the estimation result of the intensity, a numerical value of the estimated intensity may be output instead of or in addition to the intensity map 112 in the above-described example.

The time interval SI for updating the display of the intensity map 112 may be slower than the frame interval FI of the color image 60. For example, while the color image 60 is displayed in 120 frames, the display of the intensity map 112 is updated once or the like.

The specification of the kind of the object in the color image 60 may be performed using a known image recognition technique without using the object kind specification model 82. Similarly, the estimation of the intensity may be performed using a known simulation method, such as the Monte Carlo method, without using the intensity estimation model 83.

A table in which a kind of an object and a material (plastic, metal, or the like) of the object are registered may be prepared, the material of the object of which the kind is specified may be derived from the table, and information regarding the derived material may be included in the reference information 111. An object is likely to absorb or scatter the radiation R depending on the material, and thus, in a case where information regarding the material is included in the reference information 111, there is a high possibility that more accurate estimation of intensity can be performed.

Second Embodiment

In the above-described first embodiment, although the intensity map 112 is displayed through the display 32, the present disclosure is not limited thereto.

Figure 21:
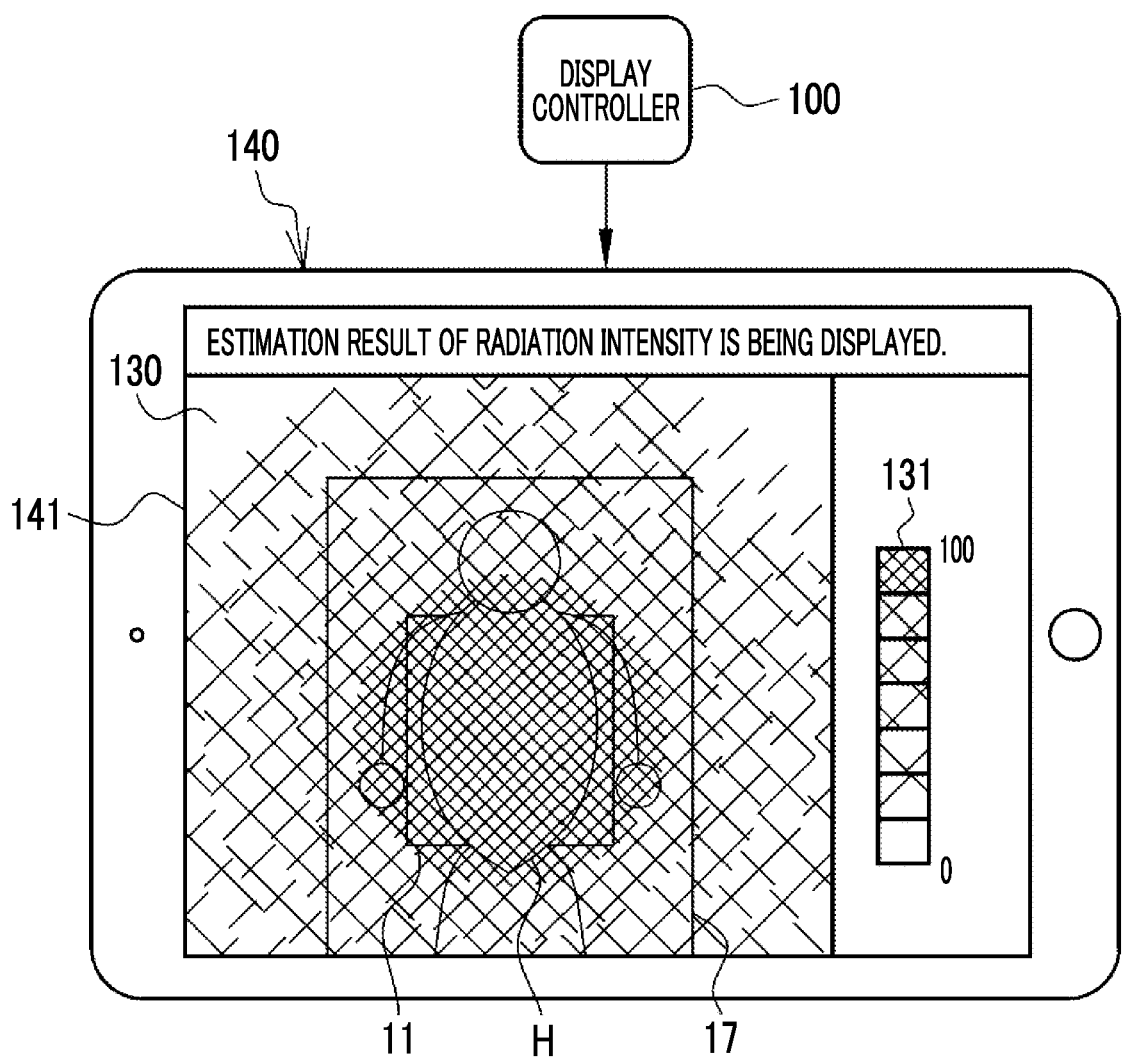
FIG. 21 is a diagram showing a second embodiment in which the superimposed image is displayed on a tablet terminal carried with the operator.

As shown in FIG. 21, the display controller 100 displays the superimposed image 130 of the color image 60 and the intensity map 112 through a display 141 of a tablet terminal 140 carried by the operator OP. The tablet terminal 140 is an example of a "terminal" according to the technique of the present disclosure. The terminal is not limited to the tablet terminal 140, and may be a smartphone, a laptop personal computer, or the like.

In this way, in the second embodiment, the display controller 100 displays the intensity map 112 through the display 141 of the tablet terminal 140 carried by the operator OP. For this reason, as long as the operator OP carries the tablet terminal 140, even in a state in which the operator OP is away from the front of the display 32 for positioning and cannot view the intensity map 112 with the display 32, it is possible to allow the operator OP to view the intensity map 112 with the display 141.

The superimposed image 130 may not be displayed on the display 32, and the superimposed image 130 may be displayed only on the display 141.

Third Embodiment

Figure 22:
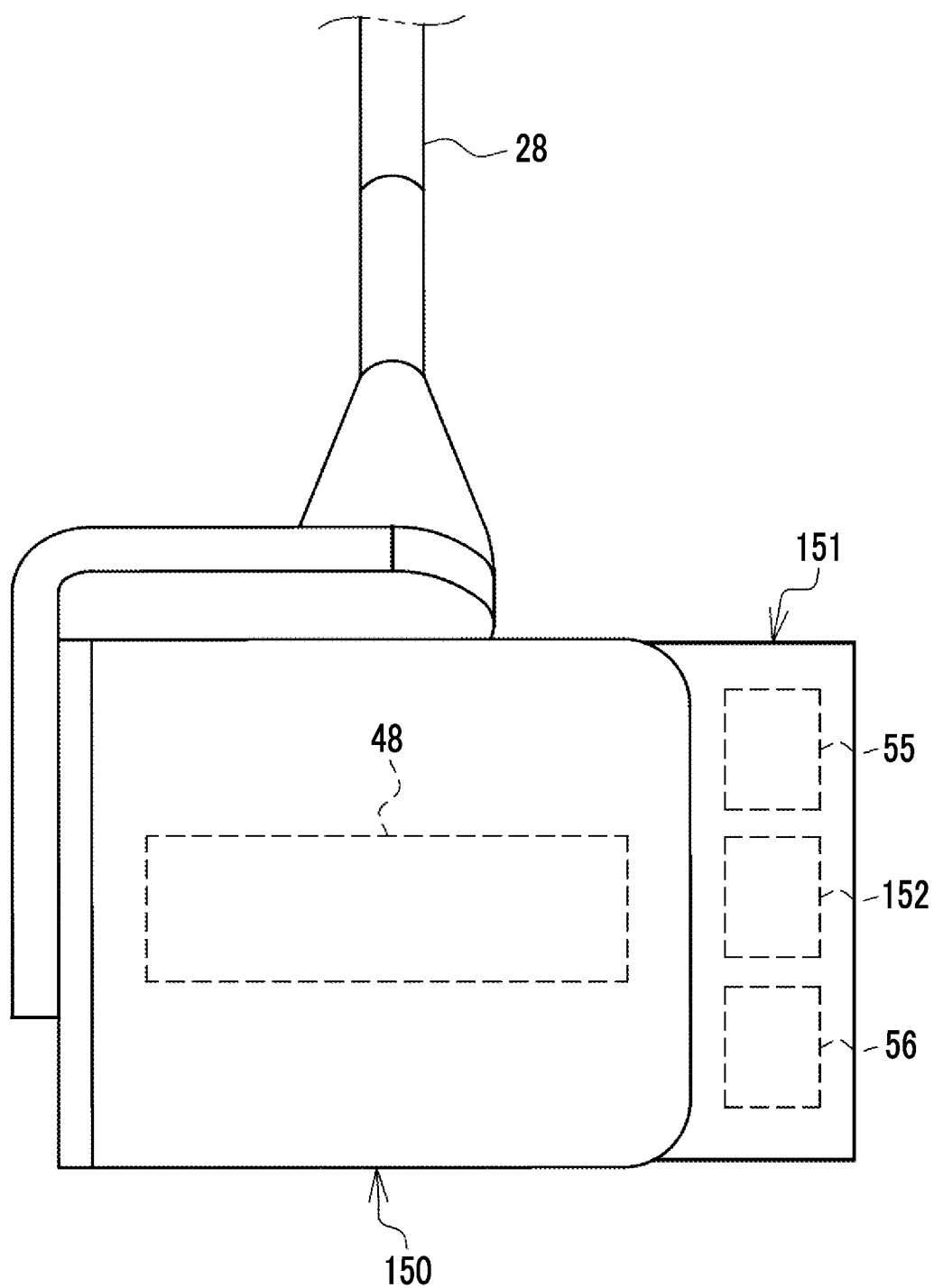
FIG. 22 is a diagram showing a camera unit of a third embodiment in which a projector is incorporated.
Figure 23:
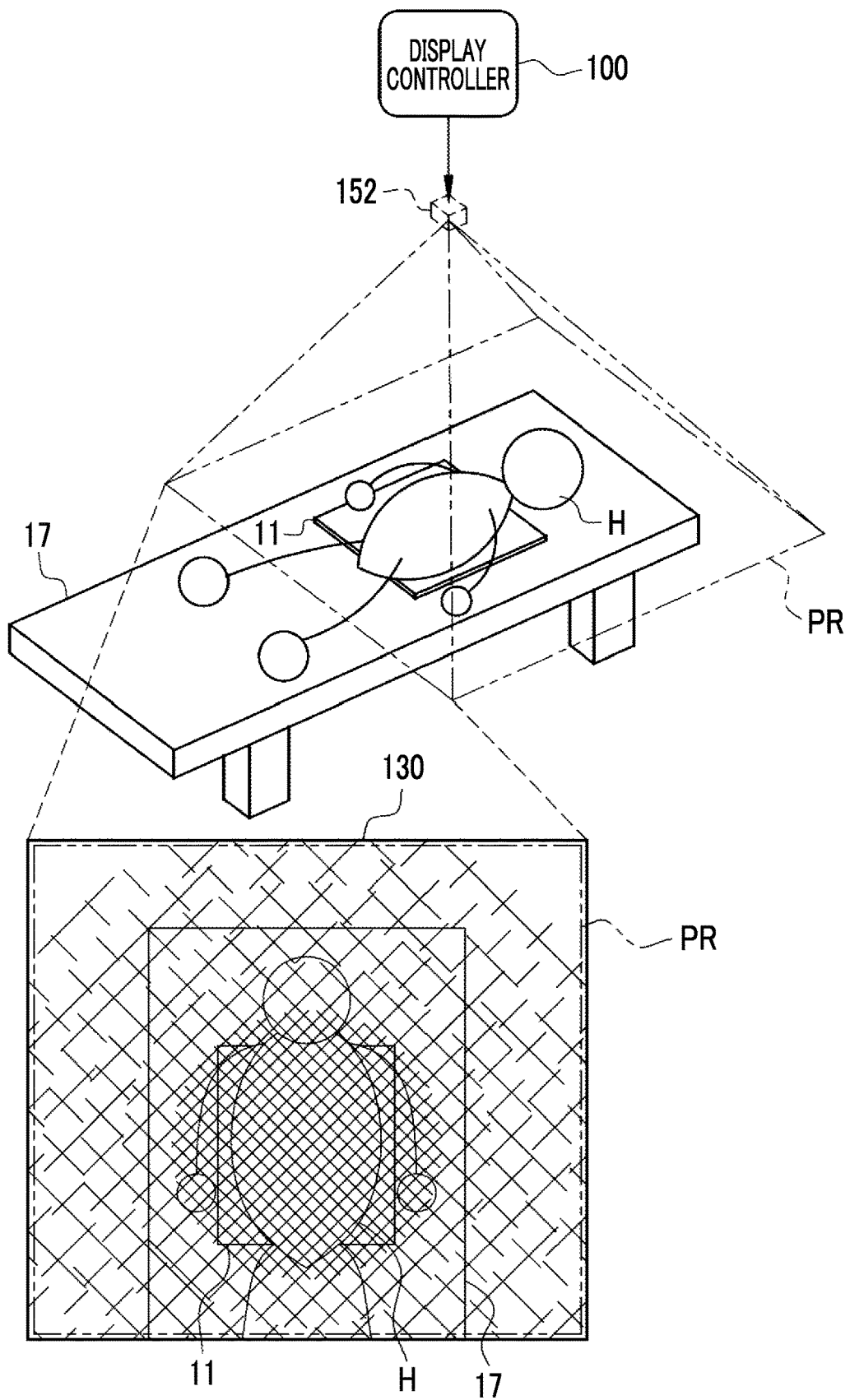
FIG. 23 is a diagram showing the third embodiment in which the superimposed image is projected from the projector in a projection range identical to an imaging range of a visible light camera and a TOF camera.

In a third embodiment shown in FIGS. 22 and 23, the superimposed image 130 of the color image 60 and the intensity map 112 is displayed through a projector 152.

In FIG. 22, a projector 152 is incorporated in a camera unit 151 of a radiation generation unit 150 of the third embodiment in addition to the visible light camera 55 and the TOF camera 56.

As shown in FIG. 23, the display controller 100 makes the projector 152 project the superimposed image 130 in a projection range PR identical to the imaging range SR of the visible light camera 55 and the TOF camera 56.

In this way, in the third embodiment, the intensity map 112 is displayed through the projector 152. For this reason, it is possible to widely notify not only a person who can view the display 32 but also a person in the periphery of the patient H of the intensity map 112. Furthermore, the superimposed image 130 is projected in the projection range PR identical to the imaging range SR of the visible light camera 55 and the TOF camera 56, whereby it is possible to enable recognition of an actual intensity of a region at first glance.

The above-described second embodiment may be applied, and the superimposed image 130 may be displayed on the display of the terminal carried by the operator OP. Alternatively, the superimposed image 130 may not be displayed on the display 32 and the display of the terminal carried by the operator OP, and the superimposed image 130 may be displayed only through the projector 152.

A screen onto which the superimposed image 130 is projected may be a whiteboard, a wall of a room, or the like. The projector 152 may be provided in, for example, the center portion 26, the column portion 27, the arm portion 28, or the like, not in the radiation generation unit 150. The projector 152 may be provided separately from the mobile radiation generation apparatus 10.

Fourth Embodiment

In the above-described first embodiment, although an example where the display of the intensity map 112 is updated at the predetermined time interval SI has been exemplified, the present disclosure is not limited thereto.

Figure 24:
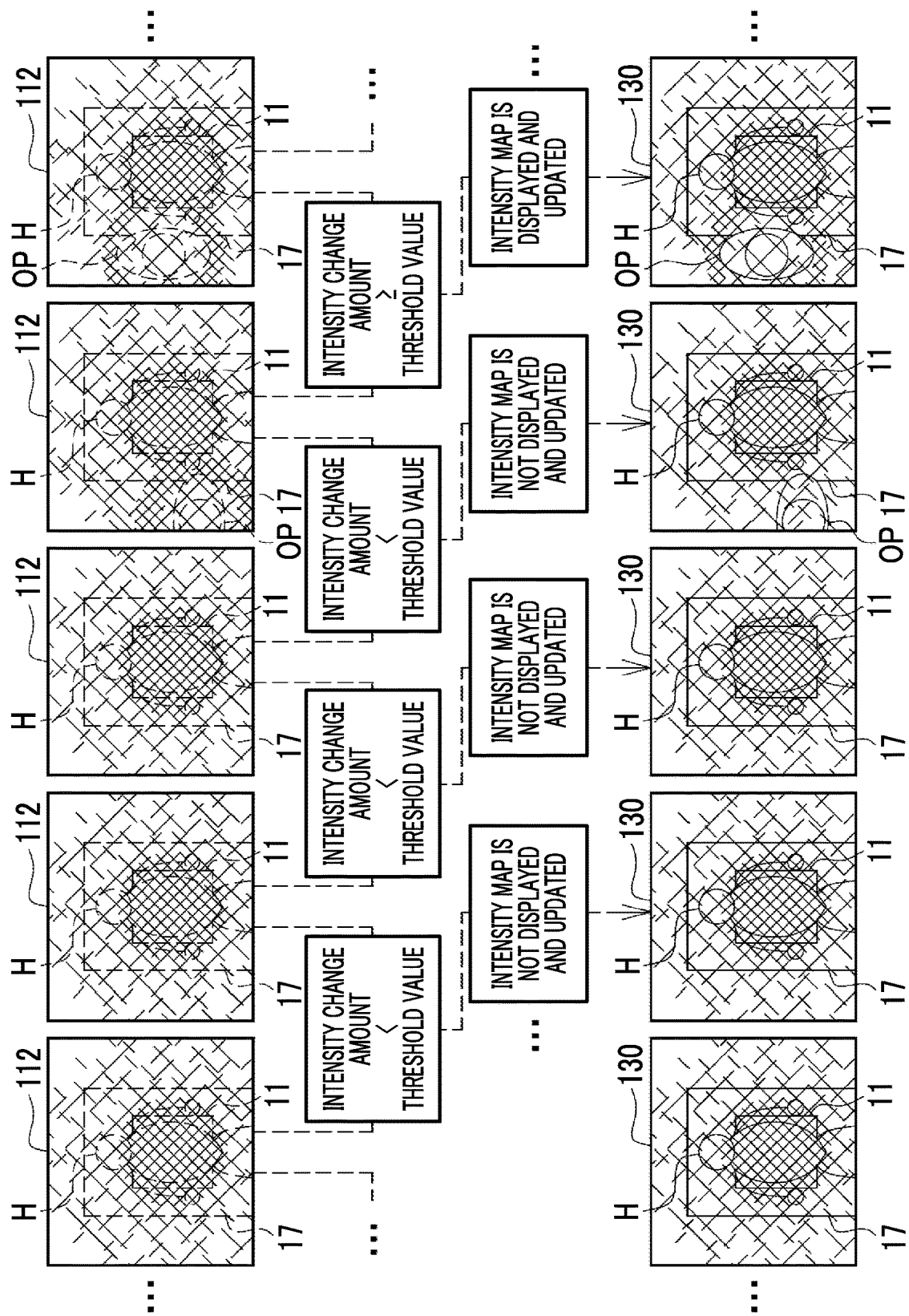
FIG. 24 is a diagram showing a fourth embodiment in which display of the intensity map is not updated in a case where an amount of temporal change of estimated intensity is less than a predetermined threshold value, and the display of the intensity map is updated in a case where the amount of change is equal to or greater than the threshold value.

As shown in FIG. 24, in a case where an amount of temporal change (hereinafter, abbreviated as an intensity change amount) of the estimated intensity is less than a predetermined threshold value (intensity change amount<threshold value), the display controller 100 does not update the display of the intensity map 112 of the superimposed image 130. On the other hand, in a case where the intensity change amount is equal to or greater than the threshold value (intensity change amount≥threshold value), the display controller 100 updates the display of the intensity map 112 of the superimposed image 130. The intensity change amount is, for example, an average value of differences obtained by calculating a difference between previous intensity and present intensity for each divided region 125 and dividing a sum of absolute values of the calculated differences by the total number of divided regions 125.

In FIG. 24, as in the case of FIG. 19, a case where the operator OP appears from the right foot side of the patient H and stands on the right chest side of the patient H is illustrated. Until the operator OP stands on the right chest side of the patient H, the intensity change amount is less than the threshold value, and thus, the display of the intensity map 112 is not updated. When the operator OP stands on the right chest side of the patient H, the intensity change amount is equal to or greater than the threshold value, and thus, the display of the intensity map 112 is updated.

In this way, in the fourth embodiment, the display controller 100 does not update the display of the intensity map 112 in a case where the intensity change amount is less than the threshold value, and updates the display of the intensity map 112 in a case where the intensity change amount is equal to or greater than the threshold value. For this reason, it is possible to prevent the display of the intensity map 112 from being rapidly updated overreacting changes in the circumstances in the periphery of the patient H.

A configuration may be made to select whether the display of the intensity map 112 is updated at the predetermined time interval SI or the display of the intensity map 112 is updated according to the intensity change amount.

Fifth Embodiment

Figure 25:
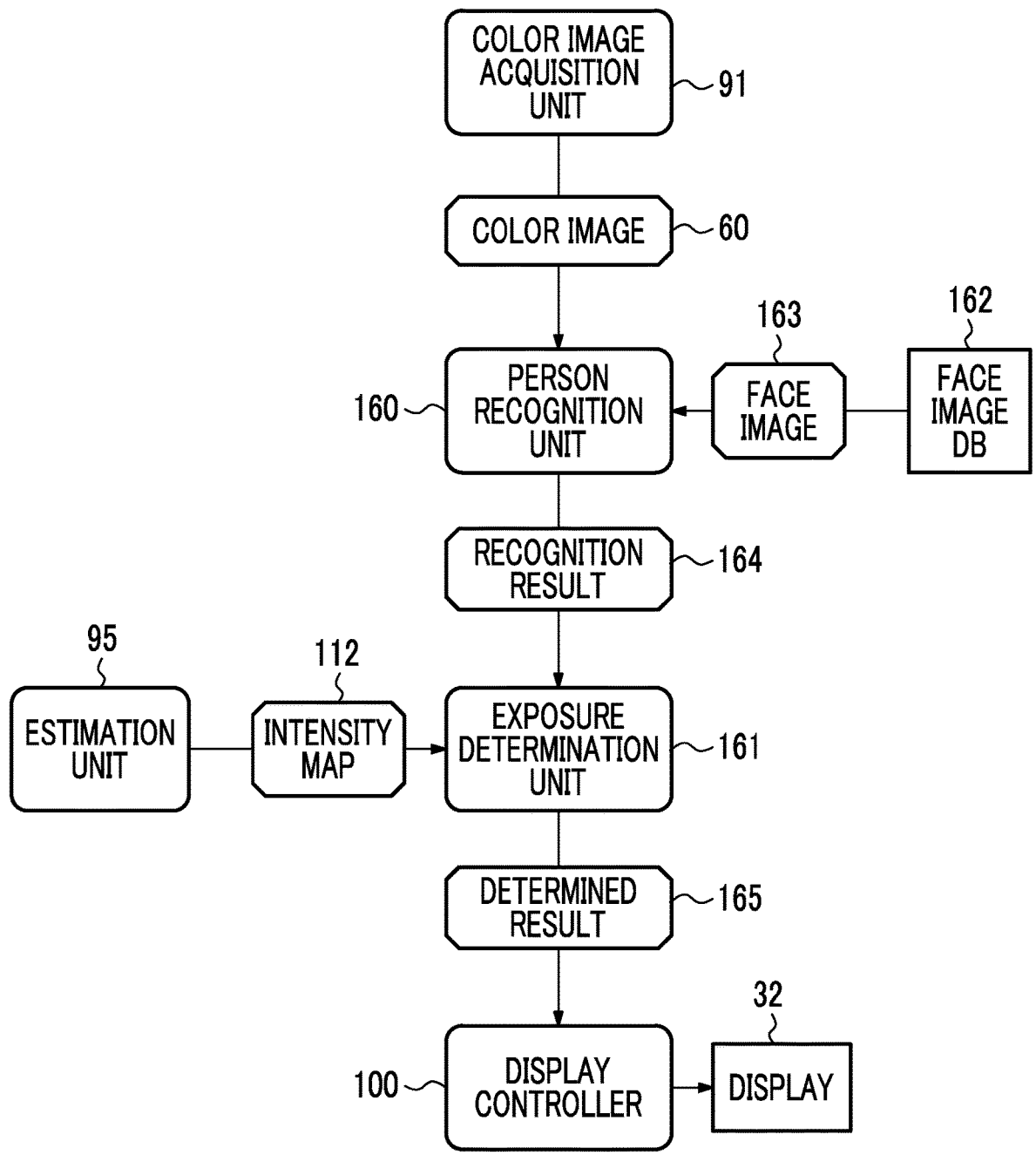
FIG. 25 is a block diagram showing functions of processing units of the CPU of the console of a fifth embodiment.
Figure 26:
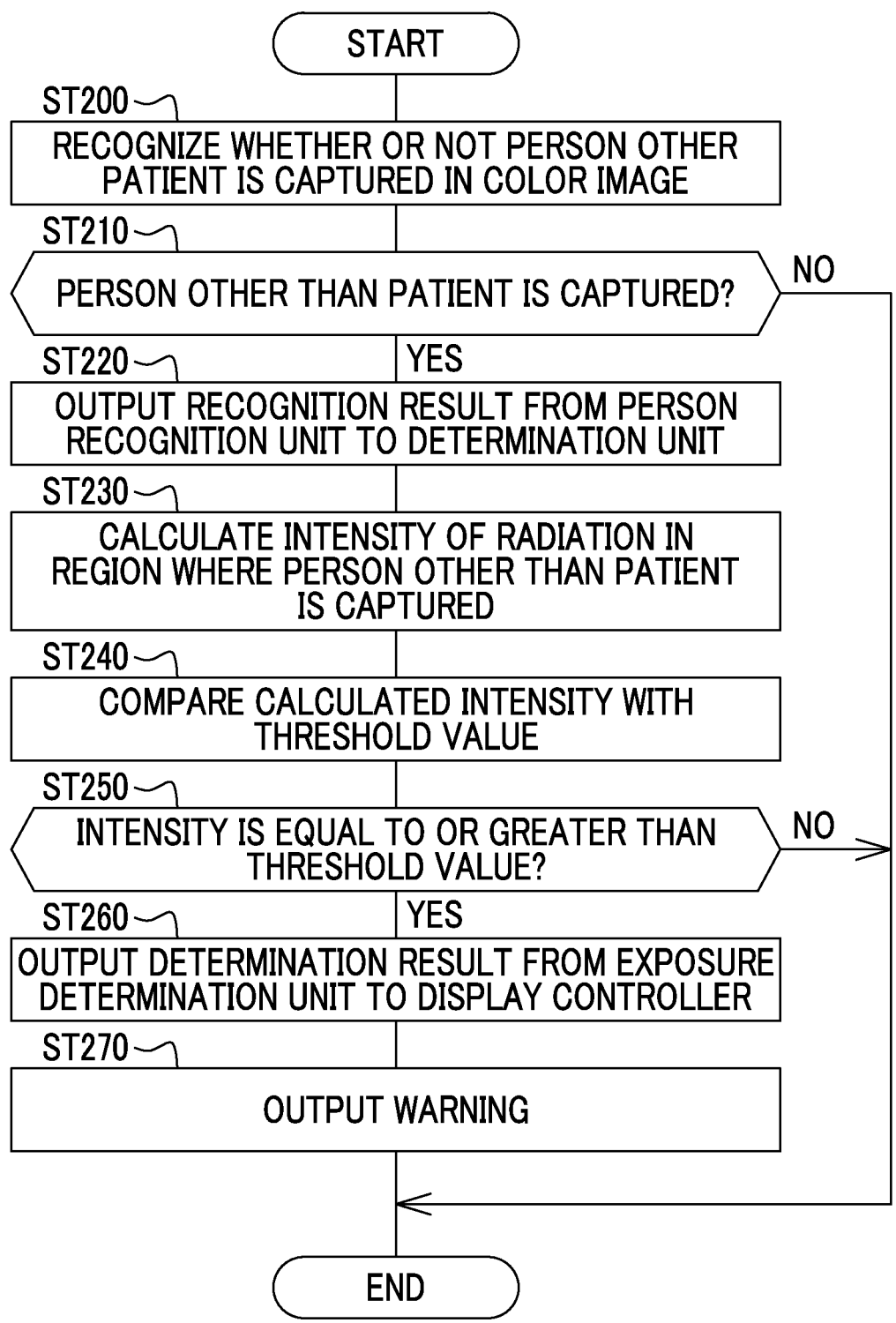
FIG. 26 is a flowchart showing a processing procedure of the fifth embodiment.
Figure 27:
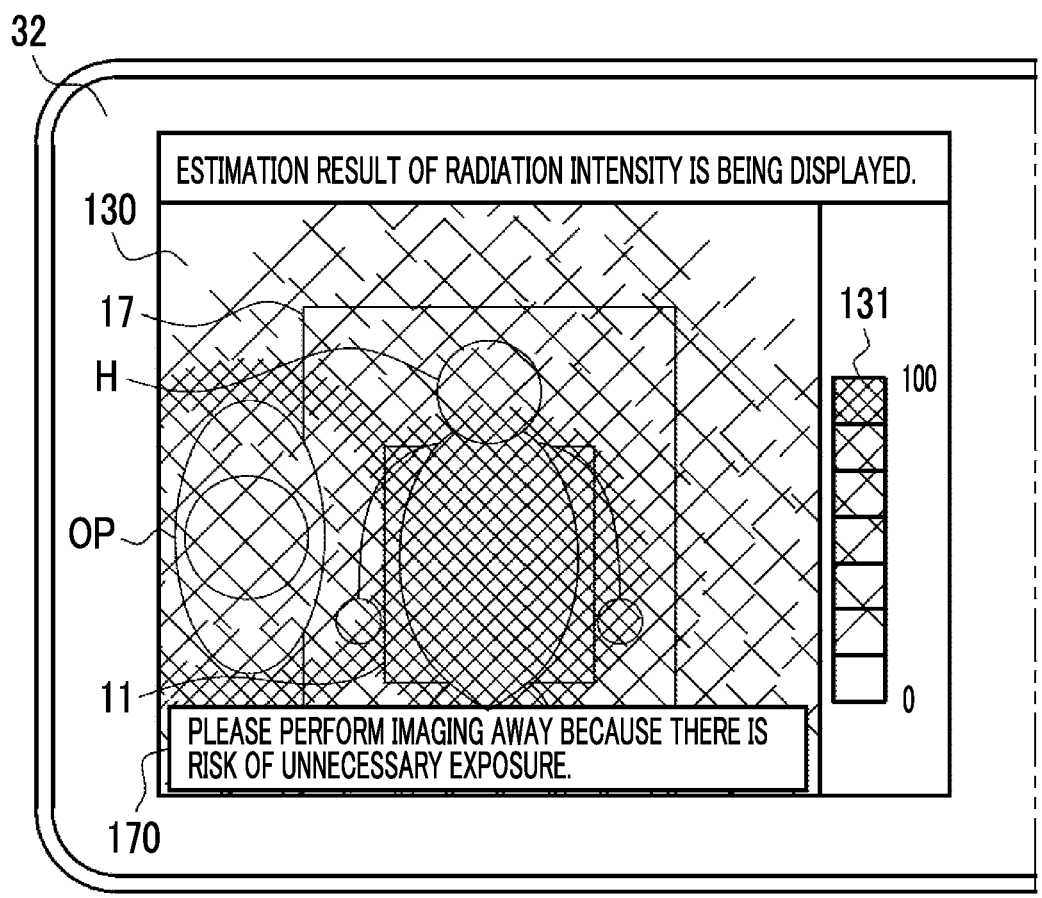
FIG. 27 is a diagram showing a manner in which a warning message is displayed on the superimposed image.

In a fifth embodiment shown in FIGS. 25 to 27, a warning is output in a case where a person other than the patient H is present in a region where the estimated intensity is equal to or greater than the predetermined threshold value.

In FIG. 25, a CPU of a console of the fifth embodiment functions as a person recognition unit 160 and an exposure determination unit 161 in addition to the processing units 90 to 100 (in FIG. 25, the units other than the color image acquisition unit 91, the estimation unit 95, and the display controller 100 are not shown) in the above-described first embodiment.

A face image database (hereinafter, abbreviated as a face image database (DB)) 162 is connected to the person recognition unit 160. In the face image DB 162, a face image 163 of the patient H is registered in advance. The person recognition unit 160 receives the face image 163 of the patient H for radiography from the face image DB 162. As also shown in FIG. 26, the person recognition unit 160 recognizes whether or not a face other than the face image 163 received from the face image DB 162 is captured, that is, whether or not a person other than the patient H is captured in the color image 60 from the color image acquisition unit 91 using a known face recognition technique (Step ST200). In a case where the person recognition unit 160 recognizes that a person other than the patient H is not captured (only the patient H is captured) (in Step ST210, NO), the person recognition unit 160 does nothing. On the other hand, in a case where the person recognition unit 160 recognizes that a person other than the patient H is captured (in Step ST210, YES), the person recognition unit 160 outputs, to the exposure determination unit 161, information to the effect that a person other than the patient H is captured and a region where the person is captured, as a recognition result 164 (Step ST220).

In a case where the recognition result 164 is received from the person recognition unit 160, the exposure determination unit 161 acquires the intensity of the divided region 125 corresponding to the region where the person other than the patient H is captured, based on the intensity map 112 from the estimation unit 95. The exposure determination unit 161 calculates an average value of the acquired intensity (Step ST230). Then, the calculated average value of the intensity is compared with a preset threshold value (Step ST240). In a case where the average value of the intensity is less than the threshold value (in Step ST250, NO), the exposure determination unit 161 does nothing. On the other hand, in a case where the average value of the intensity is equal to or greater than the threshold value (in Step ST250, YES), the exposure determination unit 161 outputs, to the display controller 100, a determination result 165 to the effect that the average value of the intensity is equal to or greater than the threshold value (Step ST260).

In a case where the determination result 165 is received from the exposure determination unit 161, the display controller 100 outputs a warning through the display 32 (Step ST270). Specifically, as shown in FIG. 27, a warning message 170 "Please perform imaging away because there is risk of unnecessary exposure" is displayed in a lower portion of the superimposed image 130. In FIG. 27, the operator OP is exemplified as the person other than the patient H.

In this way, in the fifth embodiment, the display controller 100 outputs the warning message 170 in a case where a person other than the patient H is present in a region where the intensity estimated in the estimation unit 95 is equal to or greater than the predetermined threshold value. For this reason, it is possible to allow a person other than the patient H to take behavior for avoiding careless exposure more positively, and to make a significant contribution to preventing careless exposure of a person other than the patient H.

A person who is present in the irradiation range IR of the radiation R may be recognized as the patient H, and a person who is present outside the irradiation range IR may be recognized as a person other than the patient H. A name tag may be put on the patient H, and the patient H may be recognized by character recognition of the name on the name tag. The patient H may be recognized by a color of a patient gown.

A static image of the intensity map 112 may be displayed at a predetermined timing, such as in a case where an instruction of the operator OP is issued.

In the above-described embodiments, although the operator OP has been exemplified as a person other than the patient H, the present disclosure is not limited thereto. A person other than the patient H also includes a medical worker other than the operator OP, a cleaner, a guard, an attendant of the patient H, and the like.

Although the patient H has been exemplified as an imaging target, the present disclosure is not limited thereto. A pet, such as a dog or a cat, or a domestic animal, such as a horse or cattle, may be an imaging target.

In the above-described embodiments, although the visible light camera 55 and the TOF camera 56 are provided in the radiation generation unit 15, the present disclosure is not limited thereto. The visible light camera 55 and the TOF camera 56 may be provided in an upper portion of a pillar of a room, on a ceiling of a room, or the like. Alternatively, a handheld camera, a tablet terminal, a smartphone, or the like carried by the operator OP may be used as the visible light camera 55. Note that, in these cases, the positional relationship between the visible light camera 55 and the TOF camera 56, and the radiation tube 48 are not constantly the same as in the above-described embodiments. For this reason, there is a need to detect the position of the radiation tube 48 with respect to the visible light camera 55 and the TOF camera 56, and to input detected positional information of the radiation tube 48 as the reference information 111 to the estimation unit 95. As a method that detects the position of the radiation tube 48, a method that provides a position sensor in the radiation tube 48 and detects the position of the radiation tube 48 from the color image 60 by image recognition is considered. In a case where a handheld camera, a tablet terminal, a smartphone, or the like carried by the operator OP is used as the visible light camera 55, the opening degree information 110 may be acquired from the color image 60, in which the emission opening of the irradiation field limiter 46 is captured, by image recognition.

Figure 28:
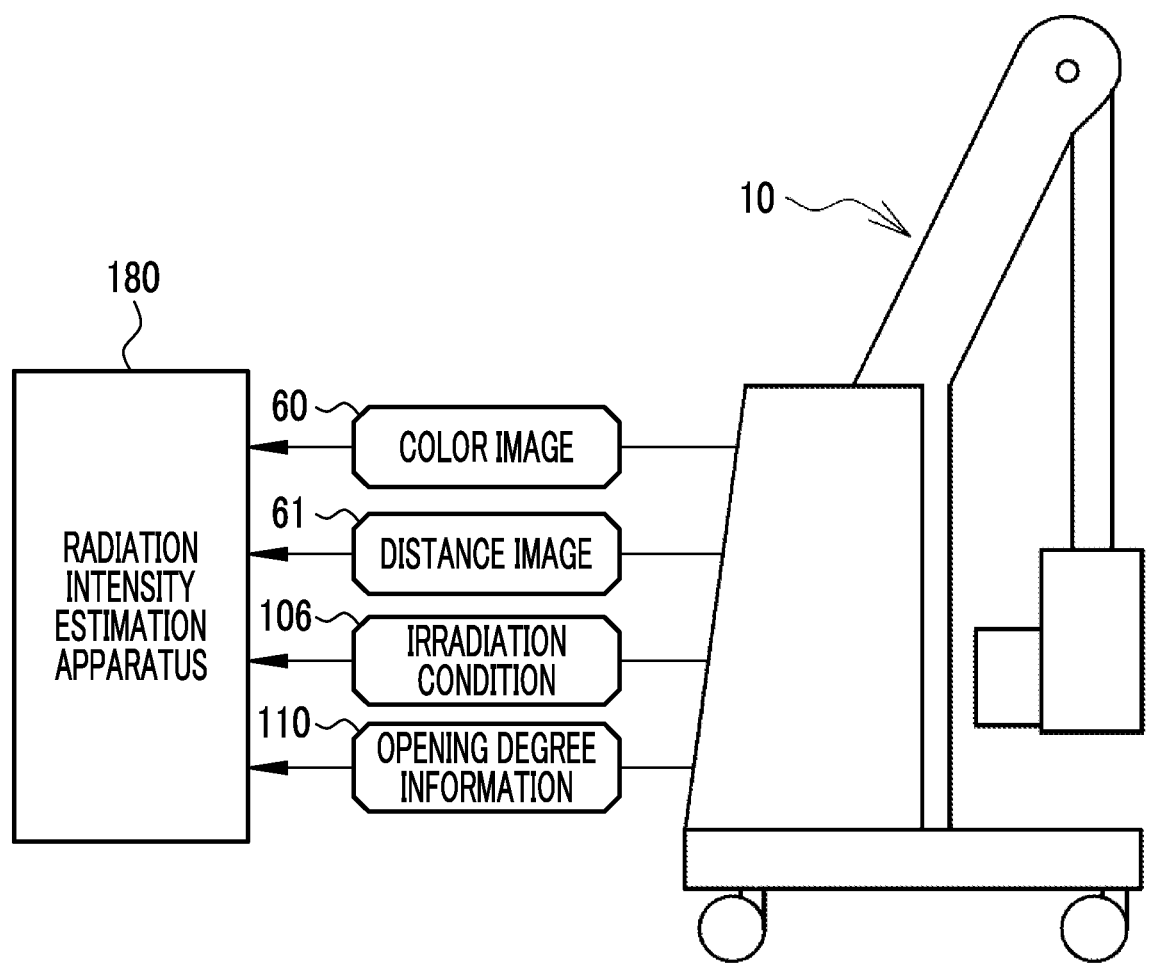
FIG. 28 is a diagram showing an aspect in which the radiation intensity estimation apparatus is provided separately from the mobile radiation generation apparatus.

In the above-described embodiments, although the console 75 of the mobile radiation generation apparatus 10 has functions of a "radiation intensity estimation apparatus" according to the technique of the present disclosure, the present disclosure is not limited thereto. As shown in FIG. 28, a radiation intensity estimation apparatus 180 may be provided separately from the mobile radiation generation apparatus 10. In this case, the mobile radiation generation apparatus 10 transmits the color image 60, the distance image 61, the irradiation condition 106, and the opening degree information 110 to the radiation intensity estimation apparatus 180. The radiation intensity estimation apparatus 180 is, for example, a desktop personal computer.

The radiation intensity estimation apparatus 180 may be a terminal that is carried by the operator OP. In this case, the operation program 80 is installed as an application program on the terminal, and processing units, such as the color image acquisition unit 91, the distance image acquisition unit 92, the opening degree information acquisition unit 93, the specification unit 94, the estimation unit 95, and the display controller 100 are constructed in a CPU of the terminal.

In the respective embodiments, for example, the hardware structures of processing units that execute various kinds of processing, such as the reception unit 90, the color image acquisition unit 91, the distance image acquisition unit 92, the opening degree information acquisition unit 93, the specification unit 94, the estimation unit 95, the irradiation controller 96, the cassette controller 97, the radiographic image acquisition unit 98, the image processing unit 99, the display controller 100, the person recognition unit 160, and the exposure determination unit 161, various processors described below can be used. Various processors include a programmable logic device (PLD) that is a processor capable of changing a circuit configuration after manufacture, such as a field programmable gate array (FPGA), a dedicated electric circuit that is a processor having a circuit configuration dedicatedly designed for executing specific processing, such as an application specific integrated circuit (ASIC), and the like in addition to the CPU 73 that is a general-purpose processor executing software (operation program 80) to function as various processing units, as described above.

One processing unit may be configured of one of various processors described above or may be configured of a combination of two or more processors (for example, a combination of a plurality of FPGAs and/or a combination of a CPU and an FPGA) of the same type or different types. A plurality of processing units may be configured of one processor.

As an example where a plurality of processing units are configured of one processor, first, as represented by a computer, such as a client or a server, there is a form in which one processor is configured of a combination of one or more CPUs and software, and the processor functions as a plurality of processing units. Second, as represented by system on chip (SoC) or the like, there is a form in which a processor that implements all functions of a system including a plurality of processing units into one integrated circuit (IC) chip is used. In this way, various processing units may be configured using one or more processors among various processors described above as a hardware structure.

In addition, the hardware structure of various processors is, more specifically, an electric circuit (circuitry), in which circuit elements, such as semiconductor elements, are combined.

The technique of the present disclosure can also be appropriately combined with at least one of various embodiments or various modification examples described above. The technique of the present disclosure is not limited to the above-described embodiments, and various configurations can be of course employed without departing from the spirit and scope of the technique of the present disclosure. In addition to the program, the technique of the present disclosure extends to a storage medium that stores the program in a non-transitory manner.

The content of the above description and the content of the drawings are detailed description of portions according to the technique of the present disclosure, and are merely examples of the technique of the present disclosure. For example, the above description relating to configuration, function, operation, and advantageous effects is description relating to examples of configuration, function, operation, and advantageous effects of the portions according to the technique of the present disclosure. Thus, it is needless to say that unnecessary portions may be deleted, new elements may be added, or replacement may be made to the content of the above description and the content of the drawings without departing from the gist of the technique of the present disclosure. Furthermore, to avoid confusion and to facilitate understanding of the portions according to the technique of the present disclosure, description relating to common technical knowledge and the like that does not require particular description to enable implementation of the technique of the present disclosure is omitted from the content of the above description and the content of the drawings.

In the specification, "A and/or B" is synonymous with "at least one of A or B". That is, "A and/or B" may refer to A alone, B alone, or a combination of A and B. Furthermore, in the specification, a similar concept to "A and/or B" applies to a case in which three or more matters are expressed by linking the matters with "and/or".

All of the documents, patent applications, and technical standards in the specification are incorporated herein by reference to the same extent that the individual documents, patent applications, and technical standards are described specifically and independently.

What is claimed is:

1. A radiation intensity estimation apparatus that is used in a mobile radiation generation apparatus that has a radiation generation unit including a radiation tube configured to emit radiation and is movable by a carriage having wheels, and estimates an intensity of the radiation before radiography, the radiation intensity estimation apparatus comprising:
at least one processor,
wherein the processor is configured to execute
optical image acquisition processing of acquiring an optical image, in which an imaging target of the radiography and a periphery of the imaging target are captured, from a camera,
distance information acquisition processing of acquiring distance information indicating a distance between the radiation tube and an object, from a distance sensor,
specification processing of specifying a kind of the object in the optical image, and
estimation processing of estimating the intensity of the radiation in an environment captured in the optical image based on reference information including the distance information and a specification result of the kind of the object.

2. The radiation intensity estimation apparatus according to claim 1,
wherein the reference information further includes an irradiation condition of the radiation and opening degree information of an emission opening of an irradiation field limiter configured to limit an irradiation field of the radiation.

3. The radiation intensity estimation apparatus according to claim 1,
wherein the processor is configured to control display of an estimation result of the intensity.

4. The radiation intensity estimation apparatus according to claim 3,
wherein the processor is configured to display the optical image and the estimation result together.

5. The radiation intensity estimation apparatus according to claim 4,
wherein the optical image is a color image,
the estimation result is an intensity map indicating a level of the intensity of each divided region obtained by dividing the optical image, and the processor is configured to display the intensity map on the color image in a superimposed manner.

6. The radiation intensity estimation apparatus according claim 3,
wherein the processor is configured to display the estimation result through a display mounted in the mobile radiation generation apparatus and configured to display a radiographic image.

7. The radiation intensity estimation apparatus according to claim 3,
wherein the processor is configured to display the estimation result through a display of a terminal carried by an operator.

8. The radiation intensity estimation apparatus according to claim 3,
wherein the processor is configured to display the estimation result through a projector.

9. The radiation intensity estimation apparatus according to claim 3,
wherein the processor is configured to update the display of the estimation result at a predetermined time interval.

10. The radiation intensity estimation apparatus according to claim 3,
wherein the processor is configured to
not update the display of the estimation result in a case where an amount of temporal change of the estimated intensity is less than a predetermined threshold value, and
update the display of the estimation result in a case where the amount of change is equal to or greater than the threshold value.

11. The radiation intensity estimation apparatus according to claim 1,
wherein the processor is configured to output a warning in a case where a person other than the imaging target is present in a region where the estimated intensity is equal to or greater than a predetermined threshold value.

12. The radiation intensity estimation apparatus according to claim 1,
wherein the processor is configured to use a first machine learning model with the optical image as input data and the specification result of the kind of the object as output data.

13. The radiation intensity estimation apparatus according to claim 1,
wherein the processor is configured to use a second machine learning model with the reference information as input data and an estimation result of the intensity as output data.

14. A method of operating a radiation intensity estimation apparatus that is used in a mobile radiation generation apparatus that has a radiation generation unit including a radiation tube configured to emit radiation and is movable by a carriage having wheels, and estimates an intensity of the radiation before radiography, the method comprising:
an optical image acquisition step of acquiring an optical image, in which an imaging target of the radiography and a periphery of the imaging target are captured, from a camera;
a distance information acquisition step of acquiring distance information indicating a distance between the radiation tube and an object, from a distance sensor;
a specification step of specifying a kind of the object in the optical image; and
an estimation step of estimating the intensity of the radiation in an environment captured in the optical image based on reference information including the distance information and a specification result of the kind of the object.

15. A non-transitory computer-readable storage medium storing an operation program for a radiation intensity estimation apparatus that is used in a mobile radiation generation apparatus that has a radiation generation unit including a radiation tube configured to emit radiation and is movable by a carriage having wheels, and estimates an intensity of the radiation before radiography, the operation program causing a computer to function as:
an optical image acquisition unit that acquires an optical image, in which an imaging target of the radiography and a periphery of the imaging target are captured, from a camera;
a distance information acquisition unit that acquires distance information indicating a distance between the radiation tube and an object, from a distance sensor;
a specification unit that specifies a kind of the object in the optical image; and
an estimation unit that estimates the intensity of the radiation in an environment captured in the optical image based on reference information including the distance information and a specification result of the kind of the object.

16. A radiography system comprising:
a mobile radiation generation apparatus that has a radiation generation unit including a radiation tube configured to emit radiation and is movable by a carriage having wheels;
a camera that images an imaging target of radiography and a periphery of the imaging target to output an optical image;
a distance sensor that detects distance information indicating a distance between the radiation tube and an object; and
at least one processor,
wherein the processor is configured to execute, before the radiography,
optical image acquisition processing of acquiring the optical image from the camera,
distance information acquisition processing of acquiring the distance information from the distance sensor,
specification processing of specifying a kind of the object in the optical image, and
estimation processing of estimating an intensity of the radiation in an environment captured in the optical image based on reference information including the distance information and a specification result of the kind of the object.

17. The radiography system according to claim 16,
wherein the camera and the distance sensor are provided in the radiation generation unit.

18. The radiography system according to claim 16,
wherein the camera sequentially outputs the optical image in compliance with a preset frame interval, and
the distance sensor sequentially detects the distance information in compliance with a detection interval according to the frame interval and outputs the distance information.

19. The radiography system according to claim 16,
wherein the camera is a visible light camera that outputs a color image as the optical image.

20. The radiography system according to claim 16, wherein the distance sensor is a distance measurement camera that measures the distance to the object using a time-of-flight method.

\* \* \* \* \*